US007569223B2

(12) United States Patent
Fischetti et al.

(10) Patent No.: US 7,569,223 B2
(45) Date of Patent: Aug. 4, 2009

(54) **PHAGE-ASSOCIATED LYTIC ENZYMES FOR TREATMENT OF *STREPTOCOCCUS PNEUMONIAE* AND RELATED CONDITIONS**

(75) Inventors: Vincent A. Fischetti, West Hempstead, NY (US); Jutta M. Loeffler, New York, NY (US); Daniel Nelson, New York, NY (US)

(73) Assignee: The Rockefeller University, New York, NY (US)

( * ) Notice: Subject to any disclaimer, the term of this patent is extended or adjusted under 35 U.S.C. 154(b) by 780 days.

(21) Appl. No.: 10/869,751

(22) Filed: Jun. 16, 2004

(65) Prior Publication Data

US 2005/0208038 A1 Sep. 22, 2005

Related U.S. Application Data

(63) Continuation-in-part of application No. 10/805,534, filed on Mar. 22, 2004, now abandoned.

(51) Int. Cl.
*A61K 38/46* (2006.01)
*A61K 38/48* (2006.01)

(52) U.S. Cl. ............ 424/94.63; 424/94.1; 424/9.1; 514/2; 530/350; 435/253.4; 536/23.2

(58) Field of Classification Search ............... 424/94.1, 424/94.63, 9.1; 536/23.2; 435/253.4; 514/2; 530/350
See application file for complete search history.

(56) References Cited

U.S. PATENT DOCUMENTS

| 3,278,378 | A  | 10/1966 | Schindler et al. |
| 3,398,056 | A  | 8/1968  | Zygmunt et al. |
| 3,594,284 | A  | 7/1971  | Zygmunt et al. |
| 4,615,697 | A  | 10/1986 | Robinson |
| 4,948,580 | A  | 8/1990  | Browning |
| 5,413,792 | A  | 5/1995  | Ninomiya et al. |
| 5,554,380 | A  | 9/1996  | Cuca et al. |
| 5,604,109 | A  | 2/1997  | Fischetti et al. |
| 5,808,022 | A  | 9/1998  | Huse |
| 5,942,243 | A  | 8/1999  | Shah |
| 5,976,862 | A  | 11/1999 | Kauffman et al. |
| 5,985,271 | A  | 11/1999 | Fischetti et al. |
| 6,017,528 | A  | 1/2000  | Fischetti et al. |
| 6,056,954 | A  | 5/2000  | Fischetti et al. |
| 6,056,955 | A  | 5/2000  | Fischetti et al. |
| 6,132,970 | A  | 10/2000 | Stemmer |
| 6,238,661 | B1 | 5/2001  | Fischetti et al. |
| 6,248,324 | B1 | 6/2001  | Fischetti et al. |
| 6,254,866 | B1 | 7/2001  | Fischetti et al. |
| 6,264,945 | B1 | 7/2001  | Fischetti et al. |

FOREIGN PATENT DOCUMENTS

WO    WO 00/32825 A2    6/2000

OTHER PUBLICATIONS

Altschul et al.; "Gapped BLAST and PSI-BLAST: a new generation of protein database search programs;" Nucleic Acids Res; 25:3389-3402 (1997).

Arkin et al., "An algorithm for protein engineering: Simulations of recursive ensemble mutagenesis," (1992) Proc. Natl. Acad. Sci. USA 89:7811-7815.
Ausubel et al., eds.; *Current Protocols in Molecular Biology*; John Wiley & Sons; title page through p. xviii, pp. 16-33 through 16-48; 1992.
Bolton, E. T. et al., "A General Method for the Isolation of RNA Complementary to DNA," (1962). Proc. Natl. Acad. Sci. USA 48:1390.
Bonner et al., "Reduction in the Rate of DNA Reassociation by Sequence Divergence," (1973). J. Mol. Biol. 81:123.
Browder et al., "Lysostaphin: Enzymatic Mode of Action," Res. Comm., 19: 393-400 (1965).
Church, G. M. et al., "Genomic sequencing," (1988). Proc. Natl. Acad. Sci. USA 81:1991-1995.
Cotton et al., "Reactivity of cytosine and thymine in single-base-pair mismatches with hydroxylamine and osmium tetroxide and its application to the study of mutations," (1985). Proc. Natl. Acad. Sci. USA 85:4397-4401.
Delgrave et al., "Recursive ensemble mutagenesis," (1993) Protein Engineering 6(3):327-331.
Dixon et al., "Lysostaphin: An Enzymatic Approach to Staphylococcal Disease. III. Combined Lysostaphin-Methicillin Therapy of Established Staphylococcal Abscesses in Mice," Yale J. Biology and Medicine, 41: 62-68 (1968).
Flavell et al., "Analysis of the β-ô-Globin Gene Loci in Normal and Hb Lepore DNA: Direct Determination of Gene Linkage and Intergene Distance," (1978). Cell 15:25.
Garcia et al., "Modular organization of the lytic enzymes of *Streptococcus pneumoniae* and its bacteriophages," Gene 86: 81-88 (1990).
Garcia et al., "Molecular evolution of lytic enzymes of *Streptococcus pneumoniae* and its bacteriophages," Proc. Natl. Acad. Sci. USA 85: 914-918 (1988).
Garcia, P. et al., "Bacteriophages of *Streptococcus pneumonia*: A Molecular Approach," Microb Drug Resist 3, 165-76 (1997).
Garcia et al.; Streptococcal Genetics (J.J. Ferretti and Curtis eds.; relevant portions: pp. 31-41, 69-72, 93-97, 143-149, 150-152, 177-180, 185-188, 189-192, 205-208, 209-211, 220-224, 225-228 and 250-258; 1987.
Gebeyehu et al., "Novel biotinylated nucleotide—analogs for labeling and colorimetric detection of DNA," Nucleic Acids Res. 15:4513-4534 1987.
Ghaffar, F. et al., "Dynamics of nasopharyngeal colonization by *Streptococcus pneumoniae*," Pediatr Infect Dis J 18, 638-46. (1999).
Gillespie, S. H. et al., "Species of Alpha-Hemolytic Streptococci Possessing a C-Polysaccharide Phosphorylcholine-Containing Antigen," Infect Immun 61, 3076-7 (1993).
Gleich, S. et al., "*Streptococcus pneumoniae* Serotype 4 Outbreak in a Home for the Aged: Report and Review of Recent Outbreaks," Infect Control Hosp Epidemiol 21, 711-7. (2000).

(Continued)

Primary Examiner—Chih-Min Kam
(74) Attorney, Agent, or Firm—Brinks Hofer Gilson & Lione

(57) ABSTRACT

The present disclosure relates to methods, compositions and articles of manufacture useful for the treatment of *Streptococcus pneumonia* bacteria and spores, and related conditions. The disclosure further relates to methods and compositions for the identification of a phage associated lytic enzyme to rapidly kill *Streptococcus pneumoniae* and other bacteria. Related articles of manufacture, methods of degrading spores and methods of treatment of infections or bacteria populations of, or subjects exposed to or at risk for exposure to, *Streptococcus pneumoniae* are also provided.

22 Claims, 8 Drawing Sheets

OTHER PUBLICATIONS

Haan, L. et al., "Nasal or intramuscular immunization of mice with influenza subunit antigen and the B subunit of *Escherichia coli* heat-labile toxin induces IgA- or IgG-mediated protective mucosal immunity," Vaccine 19, 2808-907 (2001).

Hausdorff, W.P., "Which Pneumococcal Serogroups Cause the Most Invasive Disease: Implications for Conjugate Vaccine Formulation and Use, Part I," Clin. Infect. Dis. 30 100-21 (2000).

Heikkinen, T. et al., "A single intramuscular dose of ceftriaxone changes nasopharyngeal bacterial flora in children with acute otitis media," Acta Paediatr 89, 1316-21. (2000).

Ike et al., "Solid phase synthesis of polynucleotides. VIII. Synthesis of mixed oligodeoxyribonucleotides by the phosphotriester solid phase method," (1983) Nucleic Acid Res. 11:477.

Itakura et al., "Expression in *Escherichia coli* of a Chemically Synthesized Gene for the Hormone Somatostatin," (1984) Science 198:1056.

Itakura et al., "Synthesis and Use of Synthetic Oligonucleotides," (1984) Annu. Rev. Biochem. 53:323.

Karlin et al., "Applications and statistics for multiple high-scoring segments in molecular sequences," Proc. Natl. Acad. Sci. USA, 90:5873-5877 (1993).

Lewin, B., *Genes V*, Oxford University Press Chapter 1, pp. 9-13, 1994.

Loeffler, J. M. et al., "Phage Lytic Enzyme Cpl-1 as a Novel Antimicrobial for Pneumococcal Bacteremia," Infection and Immunity, Nov. 2003, pp. 6199-6204.

Loeffler, J. M. et al., "Rapid Killing of *Streptococcus pneumoniae* with a Bacteriophage Cell Wall Hydrolase," Science, vol. 294, Dec. 7, 2001, pp. 2170-2172.

Loeffler, J. M. et al., "Synergistic Lethal Effect of a Combination of Phage Lytic Enzymes with Different Activities on Penicillin-Sensitive and -Resistant *Streptococcus pneumoniae* Strains," Antimicrobial Agents and Chemotherapy, Jan. 2003, pp. 375-377.

Loessner, et al., "Evidence for a Holin-Like Protein Gene Fully Embedded Out of Frame in the Endolysin Gene of *Staphylococcus aureus* Bacteriophage 187," Journal of Bacteriology, Aug. 1999, p. 4452-4460.

Loessner, M. J., "Heterogeneous endolysins in *Listeria monocytogenes* bacteriophages: a new class of enzymes and evidence for conserved holin genes within the siphoviral lysis cassettes," Mol Microbiol 16, 1231-41. (1995).

Lopez et al., "Structural analysis and biological significance of the cell wall lytic enzymes of *Streptococcus pneumoniae* and its bacteriophage," FEMS Microbiol. Lett. 100: 439-448 (1992).

Lopez et al., "The Pneumococcal Cell Wall Degrading Enzymes: A Modular Design to Create New Lysins?," Microbial Drug Resistance 3: 199:211 (1997).

Mbelle, N. et al., "Immunogenicity and Impact on Nasopharyngeal Carriage of a Nonavalent Pneumococcal Conjugate Vaccine," J Infect Dis 180, 1171-6. (1999).

Melander, E. et al., "Previous Antibiotic Consumption and Other Risk Factors for Carriage of Penicillin-Resistant *Streptococcus pneumoniae* in Children," Eur J Clin Microbiol Infect Dis 17, 834-8. (1998).

Morita, J. Y. et al., "Impact of azithromycin on cropharyngeal carriage of Group A Streptococcus and nasopharyngeal carriage of macrolide-resistant *Streptococcus pneumoniae*," Pediatr Infect Dis J 19, 41-6. (2000).

Myers et al., "Detection of Single Base Substitutions by Ribonuclease Cleavage at Mismatches in RNA:DNA Duplexes," (1985). Science 230:1242.

Myers et al., "Recent Advances in the Development of Methods for Detecting Single-base Substitutions Associated with Human Genetic Diseases," (1986). Cold Spring Harbor Symp. Quant. Biol. 51:275-284.

Narang, "DNA Synthesis," Tetrahedron Report No. 140, (1983) Tetrahedron 39:3.

Nelson, D. et al., "Prevention and elimination of upper respiratory colonization of mice by group A streptococci by using a bacteriophage lytic enzyme," PNAS, vol. 98, No. 7, Mar. 27, 2001, pp. 4107-4112.

Pelton, S. I., "Acute otitis media in the era of effective pneumococcal conjugate vaccine: will new pathogens emerge?," Vaccine 19 Suppl 1, S96-9. (2000).

Putnam, S. D., "Pharyngeal colonization prevalence rates for *Streptococcus pyogenes* and *Streptococcus pneumoniae* in a respiratory chemoprophylaxis intervention study using azithromycin," Clin Microbiol Infect 6, 2-8. (2000).

Recsei et al., "Cloning, sequence, and expression of the lysostaphin gene from *Staphylocuccus simulans*," Proc. Natl. Acad. Sci. USA, 84: 1127-1131 (1987).

Roberts, R. B., "Penicillin-Resistant *Streptococcus pneumoniae* in Metropolitan New York Hospitals: Case Control Study and Molecular Typing of Resistant Isolates," Microb Drug Resist 7, 137-52. (2001).

Robinson, K. A. et al., "Epidemiology of Invasive *Streptococcus pneumoniae* infections in the United States, 1995-1998," JAMA 285, 1729-35. (2001).

Romero et al., "Sequence of the *Streptococcus pneumoniae* Bacteriophage HB-3 Amidase Reveals High Homology with the Major Host Autolysin," J. Bacteriol. 172: 5064-5070 (1990).

Ronda et al., "Biological role of the pneumococcal amidase: Cloning of the *lytA* gene in *Streptococcus pneumoniae*," Eur. J. Biochem. 164: 621-624 (1987).

Sa-Leao, R. et al., "Carriage of Internationally Spread Clones of *Streptococcus pneumoniae* with Unusual Drug Resistance Patterns in Children Attending Day Care Centers in Lisbon, Portugal," J Infect Dis 182, 1153-60. (2000).

Sambrook et al. (1989), *Molecular Cloning: A Laboratory Manual*, Cold Spring Harbor, N.Y., chapters 9 and 11.

Sanchez et al., 3'-End modifications of the *Streptococcus pneumoniae lytA* gene: role of the carboxy terminus of the pneumococcal autolysin in the process of enzymatic activation (conversion), Gene 61: 13-19 (1987).

Sanchez-Puelles, J. M., "Immobilization and single-step purification of fusion proteins using DEAE-cellulose," Eur J Biochem 203, 153-9. (1992).

Schaffner et al., "Lysostaphin: An Enzymatic Approach to Staphylococcal Disease. II. In Vivo Studies," Yale J. Biol. & Med., 39:230 (1967).

Sears et al., J. Dairy Science, 71 (Suppl. 1): 244(1988).

Sheehan, M. M., "The lytic enzyme of the pneumococcal phage Dp-1: a chimeric lysine of intergeneric origin," Mol. Microbiol 25, 717-725 (1997).

Southern, E. M., "Detection of Specific Sequences Among DNA Fragments Separated by Gel Electrophoresis," (1975). J. Mol. Biol. 98:503.

Stevenson, C. G. et al., "Prevention of influenza and pneumococcal pneumonia in Canadian long-term care facilities: How are we doing?," CMAJ 164, 1413-9. (2001).

Stoflet et al., "Genomic Amplification with Transcript Sequencing," Science 239:491-494, 1988.

Tomasz, A., "Choline in the Cell Wall of a Bacterium : Novel Type of Polymer-Linked Choline in Pneumococcus," Science 157, 694-7. (1967).

Tuomanen, E. I., :Mechanism of Phenotypic Tolerance of Nongrowing Pneumococci to Beta-Iactam Antibiotics, Scand J Infect Dis Suppl. 74, 102-12 (1991).

Wallace et al., "Application of Synthetic DNA Probes to the Analysis of DNA Sequence Variants in Man," (1986). Cold Spring Harbor Symp. Quant. Biol. 51:257-261).

Ward et al., "Enzymatic synthesis of biotin-labeled polynucleotides: Novel nucleic acid affinity probes," Proc. Natl. Acad. Sci. USA 78:6633-6657 1981.

Witte, A. et al., "Characterization of *Escherichia coli* lysis using a family of chimeric *E-L* genes," FEMS Microbiol. Lett. Jul. 1, 1998, 164(1); 159-67.

Wu, H. Y. et al., "Establishment of a *Streptococcus pneumoniae* nasopharyngeal colonization model in adult mice," Microb. Pathog. 23, 127-37 (1997).

Young, et al., "Phages will out: strategies of host cell lysis," Trends in Microbiology v. 8, No. 4, Mar. 2000.

FIG. 1
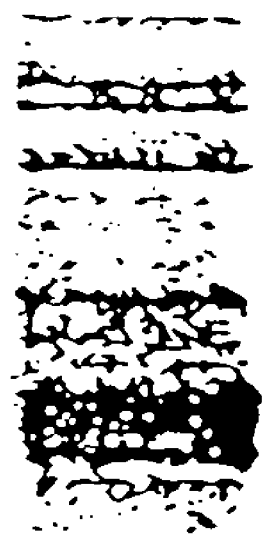
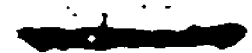
kDa     1     2
131 -
86 -
43.8 -
33 -

FIG. 5

MGVDIEKGVAWMQARKGRVSYSMDFRDGPDSYDCSSSMYYALRS
AGASSAGWAVNTEYMHAWLIENGYELISENAPWDAKRGDIFIWGRKGASAGAGGHTGM
FIDSDNIIHCNYAYDGISVNDHDERWYYAGQPYYVVYRLTNANAQPAEKKLGWQKDAT
GFWYARANGTYPKDEFEYIEENKSWFYFDDQGYMLAEKWLKHTDGNWYWFDRDGYMAT
SWKRIGESWYYFNRDGSMVTGWIKYYDNWYYCDATNGDMKSNAFIRYNDGWYLLLPDG
RLADKPQFTVEPDGLITAKV

FIG. 6

```
   1 tttaaatttt ttgacaaagt taattcaaat tgtaccgctg aagcaattt  ccatgtattc
  61 actcaaagtt gttcagtgtg gctcaatcat attaaaatcg aacttggtaa tatctctact
 121 ccttttagtg aagcagagga agaccttaaa tatcgaattg actcaaaagc cgatcaaaag
 181 ctaactaacc aacagttgac ggcactcacg gaaaaggctc aactacatga cgcagaactg
 241 aaagctaagg ctacaatgga gcagttaagt aacttagaaa aggcttatga aggtagaatg
 301 aaagctaatg aagaagctat caacaaatcg gaacccgacc taatcttagc ggcaagtcga
 361 attgaagcta ctatccaaga acttggcggg ctacgggaac tgaagaagtt cgtcgacagt
 421 tgcatgagct cttctaatca aggtctaatt atcggtaaga acgacggtag ctctaccatt
 481 aaggtatcaa gtgaccgaat ttctatgttc tccgcaggga atgaagttat gtaccttacg
 541 caagggttca ttcacatcga taacgggatc tttacccaat ccattcaagt cggccgattt
 601 agaacggaac aatactcgtt taatccagac atgaacgtga ttcggtatgt aggataagga
 661 gaataacatg acaaaattta tcaactcata cggccctctt cacttgaacc tttacgtcga
 721 acaagttagt caggacgtaa cgaacaactc ctcgcgagtt agttggcgag ctactgtcga
 781 ccgcgatgga gcttatcgaa cgtggactta tggaaatatt agtaacctt  ccgtatggtt
 841 aaatggttca agtgttcata gcagtcaccc agactacgac acgtccggcg aagaggtaac
 901 gctcgcaagt ggagaagtga ctgttcctca caatagtgac gggacaaaga caatgtccgt
 961 ttgggcttcg tttgacccta ataacggcgt tcacggaaat atcactatct ctactaatta
1021 cactttagac agtattccaa ggtctacaca gatttctagt tttgagggaa atcgaaatct
1081 aggatcttta catacggtta tctttaaccg aaaagtgaac tcttttacgc atcaagtttg
1141 gtaccgagtt ttcggtagcg actggataga tttaggtaag aaccatacta ctagcgtatc
1201 ctttacgccg tcactggact tagcaaggta cttacctaaa tcaagttccg gaacaatgga
1261 catctgtatt cgaacctata acggaactac gcaaattggt agtgacgtct attcaaacgg
1321 atggaggttc aacatccccg attcagtacg tcctactttt tcgggcattt ctttagtaga
1381 cacgacttca gcggttcgac agattttaac agggaacaac ttcctccaaa tcatgtcgaa
1441 cattcaagtc aacttcaaca atgcttccgg cgcttacgga tccactatcc aagcatttca
1501 cgctgagctc gtaggtaaaa accaagctat caacgaaaac ggcggcaaat tgggtatgat
1561 gaactttaat ggctccgcta ccgtaagagc atgggttaca gacacgcgag gaaaacaatc
1621 gaacgtccaa gacgtatcta tcaatgttat agaatactat ggaccgtcta tcaatttctc
1681 cgttcaacgt actcgtcaaa atcctgcaat tatccaagct cttcgaaatg ctaaggtcgc
1741 acctataacg gtaggaggtc aacagaaaaa catcatgcaa attaccttct ccgtggcgcc
1801 gttgaacact actaatttca cagaagatag aggttcggcg tcagggacgt tcactactat
1861 ttccctactg actaactcgt ccgcgaactt agctggtaac tacgggccgg acaagtctta
1921 catagttaag gctaaaatcc aagacaggtt cacttcgact gaattttagtg ctacggtacc
1981 taccgaatca gtagttctta actatgacaa ggacggtcga cttggagttg gtaaggttgt
2041 agaacaaggg aaggcagggt caattgatgc agcaggtgat atatatgctg gaggtcgaca
2101 agttcaacag tttcagctca ctgataataa tggagcattg aacaggggtc aatataacga
2161 tgttggaata agcgtgaaac agagtttaca tggcgaagta acaaatacga ggacaaccct
2221 acgggaactc gaggtgaatg gggactattt caaaatttct ggttagatag ctggaaaatg
2281 gttcaatcct tcattacaat gtcaggaaga atgttcatca ggacagcgaa cgatggaaac
2341 agctggagac ctaacaagtg gaaagaggtt ctatttaagc aagacttcga acagaataat
2401 tggcagaaac ttgttcttca aagtgggtgg aaccatcact caacctatgg cgacgcattc
2461 tattcgaaaa ctcttgacgg catagtatat ttgagaggaa atgtgcataa aggacttatc
2521 gacaaagagg ctactattgc agtacttcct gaaggattta gaccgaaagt ttcaatgtat
2581 cttcaggctc tcaataactc atatggaaat gccattctat gtatatacac tgacggaaga
2641 cttgtggtga atcgaatgt  agataattct tggttaaatt tagacaatgt ctcatttcgt
2701 atttaatttg agctgaaatc atgttataat attttttaga aaggaggtga gaactatgtt
2761 gaaccttaca aaatcgcgcc aaattgtggc agagttcact attggacaag gagctgaaaa
2821 gaaacttgtc aaaacaacga ttgtgaacat tgatgcaaac gcagtatcaa ccgtctctga
2881 aactcttcat gacccagact tgtatgctgc gaaccgtcga gaacttcgag ctgacgagca
2941 aaaacttcgc gaaactcgtt acgcaatcga agatgaaatt aatagctgga gcggggggaaa
3001 aaaggggag  cccggctcta acaggctgaa taaggaggcg tcaatctatg ccaatgtggc
3061 taaacgacac cgcagtcttg acgacgatta ttacagcgtg cagcggagtg cttactgtcc
3121 tactaaataa gttattcgaa tggaaatcga ataaagccaa gagcgttta  gaggatatct
3181 ctacaactct tagcactctt aaacagcagg tcgacgggat tgaccaaacg acagtagcaa
3241 tcaatcacca aaatgacgtc attcaagacg gaactagaaa aattcaacgt taccgtcttt
```

FIG. 6 (Cont'd)

```
3361 tctctatttt attcgaaagt tataagaacc ttggcggaaa tggtgaagtt gaagccttgt
3421 atgaaaaata caagaaatta ccaattaggg aggaagattt agatgaaact atctaacgaa
3481 caatatgacg tagcaaagaa cgtggtaacc gtagtcgttc cagcagcgat tgcactaatt
3541 acaggtcttg gagcgttgta tcaatttgac actactgcta tcacaggaac cattgcactt
3601 cttgcaactt ttgcaggtac tgttctagga gtttctagcc gaaactacca aaaggaacaa
3661 gaagctcaaa acaatgaggt ggaataatgg gagtcgatat tgaaaaaggc gttgcgtgga
3721 tgcaggcccg aaagggtcga gtatcttata gcatggactt tcgagacggt cctgatagct
3781 atgactgctc aagttctatg tactatgctc tccgctcagc cggagcttca agtgctggat
3841 gggcagtcaa tactgagtac atgcacgcat ggcttattga aaacggttat gaactaatta
3901 gtgaaaatgc tccgtgggat gctaaacgag gcgacatctt catctgggga cgcaaaggtg
3961 ctagcgcagg cgctggaggt catacaggga tgttcattga cagtgataac atcattcact
4021 gcaactacgc ctacgacgga atttccgtca acgaccacga tgagcgttgg tactatgcag
4081 gtcaacctta ctactacgtc tatcgcttga ctaacgcaaa tgctcaaccg gctgagaaga
4141 aacttggctg gcagaaagat gctactggtt tctggtacgc tcgagcaaac ggaacttatc
4201 caaaagatga gttcgagtat atcaagaaa acaagtcttg gttctacttt gacgaccaag
4261 gctacatgct cgctgagaaa tggttgaaac atactgatgg aaattggtat tggttcgacc
4321 gtgacggata catggctacg tcatggaaac ggattggcga gtcatggtac tacttcaatc
4381 gcgatggttc aatggtaacc ggttggatta agtattacga taattggtat tattgtgatg
4441 ctaccaacgg cgacatgaaa tcgaatgcgt ttatccgtta taacgacggc tggtatctac
4501 tattaccgga cggacgtctg gcagataaac ctcaattcac cgtagagccg gacgggctca
4561 ttactgctaa agtttaaaat atagagagga ggaagctctt ttcttaatat tgtttctctt
4621 aatcccgcaa ggtttcgacc ctgcggggtt tatgtgtcgt gaattactct atttacttat
4681 tcgaagattt caattataat taaataatca acgagattca taattggagg aatga
```

1

PHAGE-ASSOCIATED LYTIC ENZYMES FOR TREATMENT OF *STREPTOCOCCUS PNEUMONIAE* AND RELATED CONDITIONS

RELATED APPLICATIONS

This application is a continuation-in-part of U.S. application Ser. No. 10/805,534, filed Mar. 22, 2004, now abandoned, which claims the benefit of U.S. patent application Ser. No. 09/960,472, filed Sep. 21, 2001, now abandoned, and U.S. Provisional Application No. 60/324,089, filed Sep. 24, 2001, the entire content of these references are incorporated by reference.

FIELD

This application relates to methods and compositions for the prophylactic and therapeutic treatment of *Streptococcus pneumoniae* and populations or infections thereof. More particularly, in some embodiments, this application provides compositions and methods using certain bacteriophage including the amidase Pal of phage Dp-1, as well as related shuffled and chimeric lytic enzymes.

BACKGROUND

As more antibiotics have been prescribed or used at an ever increasing rate for a variety of illnesses, increasing numbers of bacteria have developed a resistance to antibiotics. Larger doses of stronger antibiotics are now being used to treat ever more resistant strains of bacteria. Multiple antibiotic resistant bacteria have consequently developed. The use of more antibiotics and the number of bacteria showing resistance has led to increasing the amount of time that the antibiotics need to be used. Broad, non-specific antibiotics, some of which have detrimental effects on the patient, are now being used more frequently. Also, antibiotics do not easily penetrate mucus linings. Additionally, the number of people allergic to antibiotics appears to be increasing. Consequently, other efforts have been sought to first identify and then kill bacteria.

The upper respiratory mucosa can serve as a reservoir for *Streptococcus pneumoniae*. Through the use of phage lytic enzymes, nasopharyngeal colonization by *S. pneumoniae* provides promising new approaches to reducing *S. pneumoniae* infection and carriage. Nasopharyngeal carriage is a major reservoir for *Streptococcus pneumoniae* in the community and a potential source of infection and infectious communication by these bacteria.

While eliminating reservoirs of *S. pneumonia* in humans and animals would reduce incidence of related infections, no intervention other than antibiotics has been available for this purpose. *Streptococcus pneumoniae* remains a significant human pathogen because of the morbidity and mortality it causes in young children, the elderly and in immunocompromised patients. *S. pneumoniae* is found in the nasopharynx of 11-76% of the population, averaging 40-50% for children and 20-30% for adults (F. Ghaffar, I. R. Friedland, G. H. McCracken, Jr., Pediatr Infect Dis J 18, 638-46. (1999), incorporated by reference). The asymptomatic carrier state, particularly in children, is thought to be the major reservoir of the pathogen, which is transmitted by salivary aerosols and direct contact. Under predisposing conditions, such as a concomitant viral infection, the organism will spread locally or systemically.

*Pneumococci* account for the majority of cases of acute otitis media (AOM), community acquired *pneumoniae* and bacterial meningitis, and can cause lethal sepsis. In recent years, resistance of *Pneumococci* to multiple antibiotics has increased worldwide. Many studies have shown that treatment with antibiotics in children, be it for AOM or eradication of group A streptococci, even with a single dose, is associated with an increase in the carriage of resistant pneumococcal strains (E. Melander, et al., Eur J Clin Microbiol Infect Dis 17, 834-8. (1998), T. Heikkinen, et al., Acta Paediatr 89, 1316-21. (2000), and J. Y. Morita, et al., Pediatr Infect Dis J 19, 41-6. (2000), all incorporated by reference). Treatment of pneumococcal disease is thus becoming more difficult than in the past. The number of annual cases of AOM in the United States is about 7 million, while invasive pneumococcal infection was recently estimated to be more than 60,000 with an overall mortality of 10%. Although most of these latter cases occurred in persons eligible for vaccination (K. A. Robinson, et al., JAMA 285, 1729-35. (2001), incorporated by reference.), vaccination rates remain insufficient (C. G. Stevenson, M. A. McArthur, M. Naus, E. Abraham, A. J. McGeer, CMAJ 164, 1413-9. (2001), S. Gleich, et al., Infect Control Hosp Epidemiol 21, 711-7. (2000) incorporated by reference). Furthermore, despite the progress that has been made with the development of conjugate vaccines for children younger than 2 years, it remains doubtful that vaccination alone is sufficient to eliminate carriage of and disease caused by *Pneumococci*. The new conjugate vaccines include a restricted number of pneumococcal serotypes and protect only incompletely against colonization with these. About one third to one half of cases of AOM are caused by strains not included in a 9-valent vaccine (S. I. Pelton, Vaccine 19 Suppl 1, S96-9. (2000), incorporated by reference). Moreover, an increase in the carriage of non-vaccine serotypes has been reported (N. Mbelle, et al., J Infect Dis 180, 1171-6. (1999), incorporated by reference). Because of these problems, there is a need for an alternative preventive strategy for situations where vaccination is insufficient, impossible or inefficient.

Eradication or even reduction of nasopharyngeal carriage is likely to reduce the transmission of *S. pneumoniae* and the incidence of infection. Antibiotic prophylaxis in controlled surroundings has shown limited success but carriers the risk of selective pressure resulting in an increase of resistant strains (S. D. Putnam, G. C. Gray, D. J. Biedenbach, R. N. Jones, Clin Microbiol Infect 6, 2-8. (2000). incorporated by reference). Until now, there has been no substance that can specifically reduce the number of *Pneumococci* carried on human mucous membranes without affecting the normal indigenous mucosal flora.

Attempts have been made to treat bacterial diseases with the use of bacteriophages. The direct introduction of bacteriophages into an animal to prevent or fight diseases has certain drawbacks. Specifically, the bacteria must be in the right growth phase for the phage to attach. Both the bacteria and the phage have to be in the correct and synchronized growth cycles. Additionally, there must be the right number of phages to attach to the bacteria; if there are too many or too few phages, there will be either no attachment or no production of the lysing enzyme. The phage must also be active enough. The phages are also inhibited by many things including bacterial debris from the organism it is going to attack. Further complicating the direct use of a bacteriophage to treat bacterial infections is the possibility of immunological reactions, rendering the phage non-functional.

Methods for obtaining and purifying bacteriophage lytic enzymes produced by bacteria infected with bacteriophage are known in the art. Recent evidence suggests that the phage enzyme that lyses the *streptococcus* organism may in limited cases actually be a bacterial enzyme that is used to construct the bacterial cell wall. While replicating in the bacterium, a phage gene product may cause the upregulation or derepression of a bacterial enzyme for the purpose of releasing the bacteriophage. These bacterial enzymes may be tightly regulated by the bacterial cell and used by the bacteria for the construction and assembly of the cell wall. In general, however, phage lytic enzymes are coded for by the phage genome and produced by the phage in the infected bacterial host for phage release.

Consequently, others have explored the use of other safer and more effective means to treat and prevent bacterial infections using bacteriophage lytic enzymes. For example, U.S. Pat. No. 5,604,109 (Fischetti et al.) relates to the rapid detection of Group A streptococci in clinical specimens, through the enzymatic digestion by a semi-purified Group C streptococcal phage associated lysin enzyme. This enzyme work became the basis of additional research, leading to methods of treating diseases. U.S. Pat. No. 5,985,271 (Fischetti and Loomis), U.S. Pat. No. 6,017,528 (Fischetti and Loomis) and U.S. Pat. No. 6,056,955 (Fischetti and Loomis) disclose the use of a lysin enzyme produced by group C streptococcal bacteria infected with a C1 bacteriophage. U.S. Pat. No. 6,056,954 (Fischetti and Loomis) discloses a method for the prophylactic and therapeutic treatment of bacterial infections with an effective amount of a lytic enzyme composition specific for the infecting bacteria, wherein the lytic enzyme is in an environment having a pH which allows for activity of said lytic enzyme; and a carrier for delivering said lytic enzyme. U.S. Pat. No. 6,238,661 (Fischetti and Loomis) discloses a method for the prophylactic and therapeutic treatment of bacterial infections in general, which comprise administering to an individual an effective amount of a composition comprising an effective amount of lytic enzyme and a carrier for delivering the lytic enzyme and the method of treating illnesses in general.

Bacteriophage lytic enzymes can also be used to treat various types of infected subjects through various routes of administration. For example, U.S. Pat. No. 6,248,324 (Fischetti and Loomis) discloses a composition for dermatological infections by the use of a lytic enzyme in a carrier suitable for topical application to dermal tissues. The method for the treatment of dermatological infections comprises administering a composition comprising an effective amount of a therapeutic agent, with the therapeutic agent comprising a lytic enzyme produced by infecting a bacteria with phage specific for that bacteria. U.S. Pat. No. 6,254,866 (Fischetti and Loomis) discloses a method for treatment of bacterial infections of the digestive tract which comprises administering a lytic enzyme specific for the infecting bacteria. The lytic enzyme is preferably in a carrier for delivering the lytic enzyme. The bacteria to be treated is selected from the group consisting of *Listeria, Salmonella, E. coli, Campylobacter*, and combinations thereof. The carrier for delivering at least one lytic enzyme to the digestive tract is selected from the group consisting of suppository enemas, syrups, or enteric coated pills. U.S. Pat. No. 6,264,945 (Fischetti and Loomis) discloses a method and composition for the treatment of bacterial infections by the parenteral introduction of at least one lytic enzyme produced by a bacteria infected with a bacteriophage specific for that bacteria and an appropriate carrier for delivering the lytic enzyme into a patient. The injection can be done intramuscularly, subcutaneously, or intravenously.

SUMMARY

This application discloses the synthesis or isolation of a variety of lytic enzymes as well as holin proteins, chimeric lytic enzymes, and shuffled lytic enzymes, and their use, for example, in the treatment of a wide variety of illnesses caused by *Streptococcus pneumoniae*. This application also provides pharmaceutical compositions comprising at least one bacteria-associated phage enzyme that is isolated from one or more bacteria species and optionally including a phage lytic enzymes and/or holin protein. For example, the lytic enzymes or holin proteins, including their isozymes, analogs, or variants, are used in an altered form. In another example the lytic enzymes or holin proteins, including their isozymes, analogs, or variants, are used in a combination of natural and altered forms. The altered forms of lytic enzymes and holin proteins are made synthetically by chemical synthesis and/or DNA recombinant techniques, and, more preferably, the enzymes are made synthetically by chimerization and/or shuffling. In yet another embodiment, the unaltered enzymes are used alone without altered enzymes. The lytic enzyme may be used in combination with holin proteins.

Other embodiments of the invention concern the isolation and use of a bacterial phage associated lytic enzymes for the treatment and prevention of *Streptococcus pneumoniae*, also referred to as pneumococcus. In one such embodiment the bacterial phage associated lytic enzyme is prepared by growing phage in an infected bacterium and harvesting the enzyme. In another such embodiment the bacterial phage associated lytic enzyme is prepared recombinantly by growing a transgenic bacterium that makes the enzyme and extracting the enzyme from the bacterium.

A phage associated lytic enzymes can be used as an active agent in a therapeutic composition, and can optionally be combined with chimeric or shuffled lytic enzymes, for example to prophylactically and therapeutically treat bacterial diseases caused by *Streptococcus pneumoniae*. A phage associated natural, shuffled and/or chimeric lytic enzyme can be administered in any suitable manner, including intravenously, to treat various conditions including septicemia and general infections of *Streptococcus pneumoniae*. Chimeric lytic enzymes can also be used to prophylactically and therapeutically treat bacterial diseases caused by *Streptococcus pneumoniae*. Holin proteins can be used in conjunction with phage associated lytic enzymes to prophylactically and therapeutically treat bacterial diseases caused by *Streptococcus pneumoniae*. Holin proteins can also be used alone to prophylactically and therapeutically treat bacterial infections caused by *Streptococcus pneumoniae*. Holin proteins can be shuffled holin proteins or chimeric holin proteins, in either combination with or independent of the lytic enzymes caused by *Streptococcus pneumoniae*.

The use of phage associated lytic enzyme produced whether natural or altered has numerous advantages for the treatment of diseases. As the phage lytic enzymes only target specific bacteria, the lytic enzymes do not interfere with normal flora. Also, phage associated lytic enzymes primarily attack cell wall structures which are not affected by plasmid variation. The actions of the lytic enzymes are fast. Yet another advantage is that the phage associated lytic enzymes can be produced by a natural process (infection of bacteria with phage) or by a synthetic process such as by recombinant means.

Methods for treating an infection are provided, the methods comprising the step of administering a composition comprising at least one lytic enzyme. The lytic enzyme can comprise an isolated polypeptide selected from the group consisting of: an isolated amino acid sequence of the polypeptide of SEQ ID NO:1, an isolated amino acid sequence having at least 80% homology to the polypeptide of SEQ ID NO:1, and an isolated amino acid sequence of the polypeptide of SEQ ID NO:1, with up to 25 amino acid substitutions.

Also provided are methods for treating an infection comprising the step of administering a composition comprising at least one lytic enzyme genetically coded for by a bacteriophage specific for *Streptococcus pneumoniae* to a subject, wherein said lytic enzyme comprises an isolated polypeptide selected from the group consisting of: an isolated amino acid sequence of the polypeptide of SEQ ID NO:1, an isolated amino acid sequence having at least 80% homology to the polypeptide of SEQ ID NO:1, and an isolated amino acid sequence of the polypeptide of SEQ ID NO:1, with up to 25 amino acid substitutions.

Further provided are methods of treating a subject exposed to or at risk for exposure to *Streptococcus pneumoniae* bacteria, the methods comprising: administering a therapeutic composition to the patient, the therapeutic composition comprising a polypeptide having at least 80% homology to the polypeptide of SEQ ID NO:1. These methods can optionally further comprise the step of identifying a subject exposed to or at risk for exposure to *Streptococcus pneumoniae*.

Also provided are methods of identifying a compound that reduces a population of *Streptococcus pneumoniae* bacteria, the method comprising: providing a bacterial population comprising *Streptococcus pneumoniae* bacteria; and contacting the bacterial population with a polypeptide having at least 80% homology to the polypeptide of SEQ ID NO:1.

Articles of manufacture are provided. For example, the articles of manufacture can comprise a vessel containing a composition comprising a polypeptide having at least 80% homology to the polypeptide of SEQ ID NO:1; and instructions for use of the composition in treatment of a patient exposed to or exhibiting symptoms consistent with exposure to *Streptococcus pneumonia* bacteria in a method comprising: identifying the patient suspected of having been exposed to *Streptococcus pneumoniae*; and administering an effective amount of the composition to the patient.

Further articles of manufacture provided comprise a packaging material and a therapeutic composition contained within the packaging material, the therapeutic composition comprising a polypeptide having at least 80% homology to the polypeptide of SEQ ID NO:1; and the packaging material comprising a label that indicates that the therapeutic composition can be used for treating a condition selected from the group consisting of: exposure to *B. anthracis* bacteria, exposure to *B. anthracis* spores, and infection by *B. anthracis* bacteria.

Also provided are methods for the prophylactic or therapeutic treatment of *Streptococcus pneumoniae*, comprising: administering to a site of infection or colonization an effective amount of at least one lytic enzyme genetically coded for by a bacteriophage specific for *Streptococcus pneumoniae*, wherein said at least one lytic enzyme is encoded by a nucleic acid that comprises a DNA having the sequence of bases 3687 to 4577 of SEQ ID No. 2 or a sequence that hybridizes with the complement of bases 3687 to 4577 of SEQ ID No. 2 under stringent hybridization conditions.

In some embodiments, the lytic enzyme is characterized by an In vitro Killing Assay comprising treatment of an exponentially growing population of *S. pneumoniae* bacteria with 100 U of the lytic enzyme for about 30 seconds that results in a decrease in the viable titer of the *S. pneumoniae* bacteria by at least $\log_{10}$ 3.0 colony forming units/ml, as compared to perfoming an In vitro Killing Assay using the enzyme buffer alone.

The lytic enzyme can be characterized by an In vitro Killing Assay comprising treatment of a stationary phase of a population of *S. pneumoniae* bacteria with 10,000 U/ml of the lytic enzyme for about 30 seconds results in a decrease in the viable titer of the *S. pneumoniae* bacteria by at least $\log_{10}$ 3.0 colony forming units/ml, as compared to perfoming an In vitro Killing Assay using the enzyme buffer alone.

The lytic enzyme can also be characterized by an In vivo Nasal Infection Assay comprising administering about $10^8$ cfu of *S. pneumoniae* bacteria, followed by administration 42 hours later of about 1400 U of the lytic enzyme results in a reduction of the *S. pneumoniae* population to less than $\log_{10}$ 0/10 μl nasal wash.

The bacteria used in the In vitro Killing Assay or the In vivo Nasal Infection can be any suitable bacteria, but are preferably selected from one or more of the group consisting of: *S. pneumoniae* DCC 1355, *S. pneumoniae* DCC 1335, *S. pneumoniae* DCC 1420, *S. pneumoniae* DCC 1476, *S. pneumoniae* DCC 1490, *S. pneumoniae* DCC 1494, *S. pneumoniae* DCC 1714, *S. pneumoniae* DCC 1808, *S. pneumoniae* DCC 1811, *S. pneumoniae* DCC 1850, *S. pneumoniae* AR 314, *S. pneumoniae* AR 620, *S. pneumoniae* GB 2017, *S. pneumoniae* GB 2092, *S. pneumoniae* GB 2163, *S. pneumoniae* R36A, and *S. pneumoniae* Lyt 4-4.

The composition administered can be a therapeutic composition that comprises a shuffled lytic enzyme, a chimeric lytic enzyme, a holin protein or a combination thereof. The therapeutic composition can further comprise a carrier, a suitable vehicle for delivery of the lytic enzyme to an infection, an antibiotic or any combination thereof.

The lytic enzyme may be specific for *S. pneumoniae*. In some embodiments, the method further comprises administering a dry anhydrous lytic enzyme.

Any suitable site of infection or colonization can be treated by the methods provided in this application. For example, the site of infection or colonization can be selected from the group consisting of: mouth, nose, throat, nasal passages, ear canal, eye, and contact lens. In some embodiments, the method is a method for treating endocarditis.

Any suitable delivery method can be used. For example, in some embodiments, the lytic enzyme can optionally be delivered parenterally, intravenously, intramuscularly, subdermally or intrathecally.

BRIEF DESCRIPTION OF THE DRAWINGS

The accompanying drawings, which are incorporated in and constitute a part of the specification, illustrate a presently preferred embodiment of the disclosure, and, together with the general description given above and the detailed description of the preferred embodiment given below, serve to explain the principles of the disclosure.

FIG. 1. is a SDS-Page analysis of the purified Pal enzyme;

FIG. 5 is an amino acid sequence listing, SEQ ID No. 1, for the Pal lytic enzyme genetically coded for by a bacteriophage specific for *Streptococcus pneumoniae*; and FIG. 6 is a nucleic acid sequence listing, SEQ ID No. 2, for the whole genome of the bacteriophage Dp1, specific for

*Streptococcus pneumoniae*, with bases 3687 to 4577 genetically coding for the Pal lytic enzyme.

Figure 7:
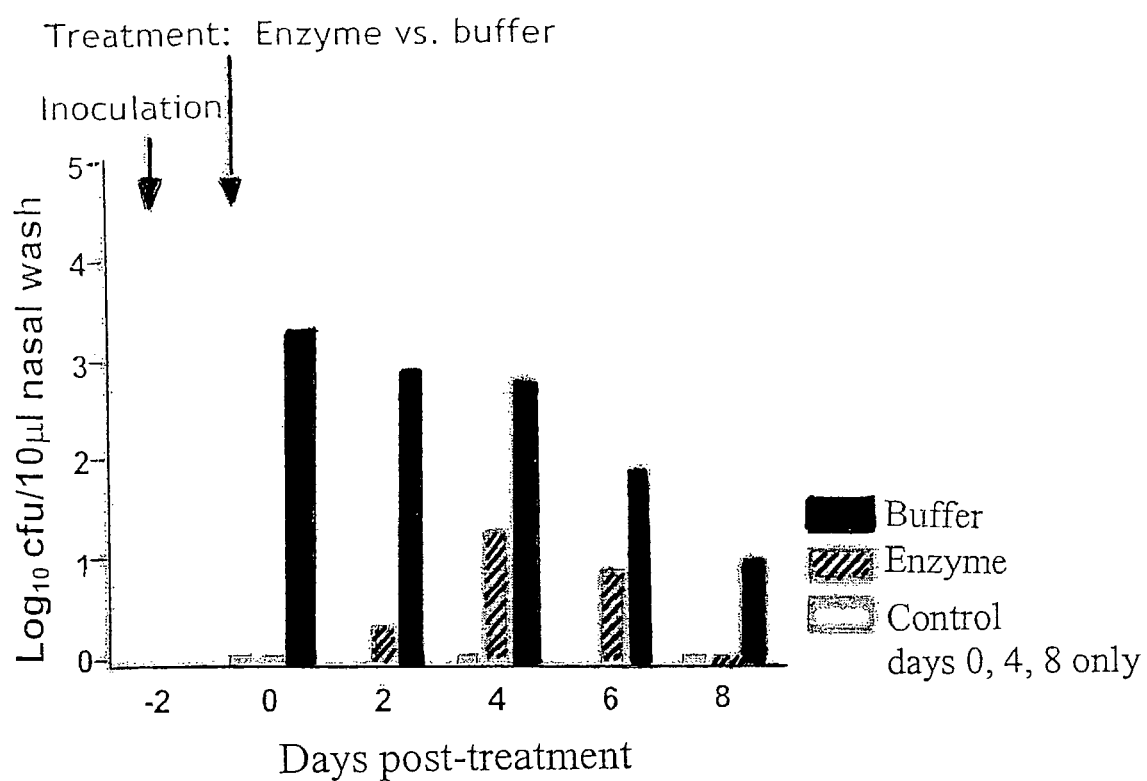

FIG. 7 is a graph showing the colonization status after a single treatment with Pal 1400 U/ml vs. buffer.

DETAILED DESCRIPTION

A "lytic enzyme" includes any bacterial cell wall lytic enzyme that kills one or more bacteria under suitable conditions and during a relevant time period. Examples of preferred lytic enzymes include, without limitation, various amidase cell wall lytic enzymes.

A "*S. pneumoniae* lytic enzyme" includes a lytic enzyme that is capable of killing one or more *Streptococcus pneumoniae* bacteria under suitable conditions and during a relevant time period.

A "bacteriophage lytic enzyme" refers to a lytic enzyme extracted or isolated from a bacteriophage or a synthesized lytic enzyme with a similar protein structure that maintains a lytic enzyme functionality.

Without being bound to theory, it is believed that a lytic enzyme specifically cleaves bonds that are present in the peptidoglycan of bacterial cells to disrupt the bacterial cell wall. It is also currently believed that the bacterial cell wall peptidoglycan is highly conserved among most bacteria, and cleavage of only a few bonds to may disrupt the bacterial cell wall. Preferably, the bacteriophage lytic enzyme is an amidase, although other enzymes can be used. Examples of lytic enzymes that cleave these bonds are various amidases such as muramidases, glucosaminidases, endopeptidases, or N-acetyl-muramoyl-L-alanine amidases. Fischetti et al (1974) reported that the C1 streptococcal phage lysin enzyme was an amidase. Garcia et al (1987, 1990) reported that the Cpl lysin from a *S. pneumoniae* from a Cp-1 phage was a lysozyme. Caldentey and Bamford (1992) reported that a lytic enzyme from the phi 6 *Pseudomonas* phage was an endopeptidase, splitting the peptide bridge formed by melodiaminopimilic acid and D-alanine. The *E. coli* T1 and T6 phage lytic enzymes are amidases as is the lytic enzyme from *Listeria* phage (ply) (Loessner et al, 1996). There are also other lytic enzymes known in the art that are capable of cleaving a bacterial cell wall.

A "lytic enzyme genetically coded for by a bacteriophage" includes a polypeptide capable of killing a host bacteria, for instance by having at least some cell wall lytic activity against the host bacteria. The polypeptide has a sequence that encompasses native sequence lytic enzyme and variants thereof. The polypeptide may be isolated from a variety of sources, such as from a bacteriophage ("phage"), or prepared by recombinant or synthetic methods, such as those by Garcia et al. Preferably, the polypeptide comprises a choline binding portion at the carboxyl terminal side and is characterized by an amidase activity to act on amide bonds in the peptidoglycan at the amino terminal side. Generally speaking, a lytic enzyme is between 25,000 and 35,000 daltons in molecular weight and comprises a single polypeptide chain; however, this can vary depending on the enzyme chain. The molecular weight most conveniently can be determined by assay on denaturing sodium dodecyl sulfate gel electrophoresis and comparison with molecular weight markers.

"A native sequence phage associated lytic enzyme" includes a polypeptide having the same amino acid sequence as an enzyme derived from a bacteria. Such native sequence enzyme can be isolated from nature or can be produced by recombinant or synthetic means.

The term "native sequence enzyme" encompasses naturally occurring forms (e.g., alternatively spliced or altered forms) and naturally-occurring variants of the enzyme. In one embodiment of the invention, the native sequence enzyme is a mature or full-length polypeptide that is genetically coded for by a gene from a bacteriophage specific for *Streptococcus pneumoniae*. Of course, a number of variants are possible and known, as acknowledged in publications such as Lopez et al., Microbial Drug Resistance 3: 199-211 (1997); Garcia et al., Gene 86: 81-88 (1990); Garcia et al., Proc. Natl. Acad. Sci. USA 85: 914-918 (1988); Garcia et al., Proc. Natl. Acad. Sci. USA 85: 914-918 (1988); Garcia et al., Streptococcal Genetics (J. J. Ferretti and Curtis eds., 1987); Lopez et al., FEMS Microbiol. Lett. 100: 439-448 (1992); Romero et al., J. Bacteriol. 172: 5064-5070 (1990); Ronda et al., Eur. J. Biochem. 164: 621-624 (1987) and Sanchez et al., Gene 61: 13-19 (1987). The contents of each of these references, particularly the sequence listings and associated text that compares the sequences, including statements about sequence homologies, are specifically incorporated by reference in their entireties.

"A variant sequence lytic enzyme" includes a lytic enzyme characterized by a polypeptide sequence that is different from that of a lytic enzyme, but retains functional activity. The lytic enzyme can, in some embodiments, be genetically coded for by a bacteriophage specific for *Streptococcus pneumoniae* having a particular amino acid sequence identity with the sequence shown as SEQ ID No. 1. For example, in some embodiments, a functionally active lytic enzyme can kill *Streptococcus pneumonia* bacteria by disrupting the cellular wall of the bacteria. An active lytic enzyme may have a 60, 65, 70, 75, 80, 85, 90, 95, 97, 98, 99 or 99.5% amino acid sequence identity with SEQ ID No. 1. Such phage associated lytic enzyme variants include, for instance, lytic enzyme polypeptides wherein one or more amino acid residues are added, or deleted at the N or C terminus of the sequence of SEQ ID No. 1. Ordinarily a phage associated lytic enzyme will have at least about 80% or 85% amino acid sequence identity with native phage associated lytic enzyme sequences, more preferably at least about 90% (e.g. 90%) amino acid sequence identity. Most preferably a phage associated lytic enzyme variant will have at least about 95% (e.g. 95%) amino acid sequence identity with the native phage associated lytic enzyme of SEQ ID No. 1.

"Percent amino acid sequence identity" with respect to the phage associated lytic enzyme sequences identified is defined herein as the percentage of amino acid residues in a candidate sequence that are identical with the amino acid residues in the phage associated lytic enzyme sequence, after aligning the sequences in the same reading frame and introducing gaps, if necessary, to achieve the maximum percent sequence identity, and not considering any conservative substitutions as part of the sequence identity.

"Percent nucleic acid sequence identity" with respect to the phage associated lytic enzyme sequences identified herein is defined as the percentage of nucleotides in a candidate sequence that are identical with the nucleotides in the phage associated lytic enzyme sequence, after aligning the sequences and introducing gaps, if necessary, to achieve the maximum percent sequence identity.

To determine the percent identity of two nucleotide or amino acid sequences, the sequences are aligned for optimal comparison purposes (e.g., gaps may be introduced in the sequence of a first nucleotide sequence). The nucleotides or amino acids at corresponding nucleotide or amino acid positions are then compared. When a position in the first sequence is occupied by the same nucleotide or amino acid as the corresponding position in the second sequence, then the molecules are identical at that position. The percent identity between the two sequences is a function of the number of identical positions shared by the sequences (i.e., % identity=# of identical positions/total # of positions×100).

The determination of percent identity between two sequences may be accomplished using a mathematical algorithm. A preferred, non-limiting example of a mathematical algorithm utilized for the comparison of two sequences is the algorithm of Karlin et al., Proc. Natl. Acad. Sci. USA, 90:5873-5877 (1993). Such an algorithm is incorporated into the NBLAST program which may be used to identify sequences having the desired identity to nucleotide sequences of the invention. To obtain gapped alignments for comparison purposes, Gapped BLAST may be utilized as described in Altschul et al., Nucleic Acids Res, 25:3389-3402 (1997). When utilizing BLAST and Gapped BLAST programs, the default parameters of the respective programs (e.g., NBLAST) may be used. See the programs provided by National Center for Biotechnology Information, National Library of Medicine, National Institutes of Health. In one embodiment, parameters for sequence comparison may be set at W=12. Parameters may also be varied (e.g., W=5 or W=20). The value "W" determines how many continuous nucleotides must be identical for the program to identify two sequences as containing regions of identity.

"Polypeptide" includes to a polymer molecule comprised of multiple amino acids joined in a linear manner. A polypeptide can, in some embodiments, correspond to molecules encoded by a polynucleotide sequence which is naturally occurring. The polypeptide may include conservative substitutions where the naturally occurring amino acid is replaced by one having similar properties, where such conservative substitutions do not alter the function of the polypeptide (see, for example, Lewin "Genes V" Oxford University Press Chapter 1, pp. 9-13 1994).

The term "altered lytic enzymes" includes to shuffled and/or chimeric lytic enzymes.

Phage lytic enzymes specific for bacteria infected with a specific phage have been found to effectively and efficiently break down the cell wall of the bacterium in question. The lytic enzyme is believed to lack proteolytic enzymatic activity and is therefore non-destructive to mammalian proteins and tissues when present during the digestion of the bacterial cell wall. As shown by Loeffler et al., "Rapid Killing of Streptococcus pneumoniae with a Bacteriophage Cell Wall Hydrolase," Science, 294: 2170-2172 (Dec. 7, 2001), and supplemental material thereto published online by Science magazine, which are incorporated herein by reference in their entirety, a purified pneumococcat bacteriophage lytic enzyme, such as Pal, is able to kill various pneumococci. Loeffler et al. have shown through these experiments that within seconds after contact, the lytic enzyme Pal is able to kill 15 clinical stains of S. pneumoniae, including the most frequently isolated serogroups and penicillin resistant stains, in vito. Treatment of mice with Pal was also able to eliminate or significantly reduce nasal carriage of serotype 14 in a dose-dependent manner. Furthermore, because it has been found that the action of Pal, like other phage lytic enzymes, but unlike antibiotics, was rather specific for the target pathogen, it is likely that the normal flora will remain essentially intact (M. J. Loessner, G. Wendlinger, S. Scherer, Mol Microbiol 16, 1231-41. (1995) incorporated herein by reference). However, various other lytic enzymes, and particularly S. pneumonia lytic enzymes, can be used in the methods, articles of manufacture and compositions disclosed herein.

One method for producing and using a S. pneumoniae lytic enzyme called Pal is presented herein as an example, however other lytic enzymes can also be prepared and used. First, E. coli DH5 a (PMSP11) expressing the amidase Pal of phage Dp-1 was obtained from R. Lopez of Center for Biological Investigations, Madrid Spain. See M M Sheehan, J. L. Garcia, R. Lopez, P. Garcia. Mol. Microbiol 25, 717-725 (1997) incorporated herein by reference. The enzyme was produced in E. coli and purified by affinity chromatography in a single step as described, with some modifications, in J. M. Sanchez-Puelles, J. M. Sanz, J. L. Garcia, E. Garcia, Eur J Biochem 203, 153-9. (1992), (incorporated herein by reference). In brief, E. coli were harvested by centrifugation, suspended in enzyme buffer (20 mM phosphate buffer (PB), 1 mM EDTA, 10 mM DTT) and broken by sonication for 1.5 min on ice. The crude extracts were ultracentrifuged (75,000×g for 1 h at 4° C.), the supernatant loaded on a DEAE-cellulose column (volume 20 ml) and washed with 3 volumes of 20 mM PB (pH 7.0), 4 volumes of PB containing 1 M NaCl, and 2 volumes of PB containing 0.1 M NaCl. The enzyme was eluted with PB containing 0.1 M NaCl and 6.5% (w/v) choline. Pooled fractions were dialyzed overnight (1:75) against enzyme buffer. Purification was verified by SDS-PAGE. Protein content was measured with the Bradford method using the dye reagent from Biorad (Hercules, Calif.). FIG. 1 shows the Page analysis 1 of the purified Pal enzyme, with lane 1 showing the crude extract from DH5-alpha, and lane 2 showing the purified Pal after affinity chromatography on DEAE cellulose.

A unit for the lytic enzyme (U) was defined using lysis of exponentially growing S. pneumoniae serogroup 14 with serial dilutions of purified Pal. S. pneumoniae strain DCC 1490 (serotype 14). The strain was grown in a brain heart infusion medium (BHI, Difco Laboratories, Detroit, Mich.) at 37° C. to logarithmic phase, centrifuged at 5000×g for 10 min at 4° C., and resuspended in sterile saline to an absorbance at 600 nm of 1.3. Pal was diluted in an enzyme buffer in serial 2-fold dilutions. In a 96-well plate, 150 ul of the bacterial suspension was incubated with 150 ul of each Pal dilution (150 ul enzyme buffer for the control well). One unit of enzyme was defined as the reciprocal of the dilution, which caused a 50% decrease in absorbance after 15 min incubation at 37° C., as compared with the absorbance of the control well. The purification process yielded an average of 15 U of enzyme per ug protein. (All chemicals were purchased from Sigma (St. Louis, Mo.) unless stated otherwise).

The killing ability of the Pal type of lytic enzyme in vitro was measured by exposing 15 clinical strains of S. pneumoniae, 2 pneumococcal mutants (R36A, Lyt 4-4) and 5 species of oral commensal streptococci (S. gordonii, S. mitis, S. mutans, S. oralis, S. salivarius) to purified enzyme at a final concentration of 100 U/ml, and in the case of the oral streptococci to 1,000 and 10,000 U/ml. The pneumococcal strains, obtained from various sources as shown in Table 1, included 9 serogroups that most frequently cause invasive disease in North America, Europe, Africa and Oceania (W. P. Hausdorff, J. Bryant, P. R. Paradiso, G. R. Siber, Clin. Infect. Dis. 30 100-21 (2000).

TABLE 1

Bacterial strains tested for susceptibility to Pal
Species/Strain/Capsular group type/Susceptibility to
Penicillin/Clonal type/Source

| | | | | | |
|---|---|---|---|---|---|
| S. pneumoniae | DCC 1355 | 19F | S | | 1 |
| S. pneumoniae | DCC 1335 | 9V | R | $Sp^9$-3 | 1 |
| S. pneumoniae | DCC 1420 | 23F | R | $Sp^{23}$-1 | 1 |
| S. pneumoniae | DCC 1476 | 15 | I | | 1 |
| S. pneumoniae | DCC 1490 | 14 | S | | 1 |
| S. pneumoniae | DCC 1494 | 14 | R | $Sp^{14}$-1 | 1 |
| S. pneumoniae | DCC 1714 | 3 | S | | 1 |
| S. pneumoniae | DCC 1808 | 24 | S | | 1 |

TABLE 1-continued

Bacterial strains tested for susceptibility to Pal
Species/Strain/Capsular group type/Susceptibility to
Penicillin/Clonal type/Source

| Species | Strain | Capsular group | Susceptibility | Source |
|---|---|---|---|---|
| S. pneumoniae | DCC 1811 | 11 | S | 1 |
| S. pneumoniae | DCC 1850 | 6B | S | 1 |
| S. pneumoniae | AR 314 | 5 | S | 1 |
| S. pneumoniae | AR 620 | 1 | S | 1 |
| S. pneumoniae | GB2017 | 18 | S | 1 |
| S. pneumoniae | GB2092 | 4 | S | 1 |
| S. pneumoniae | GB2163 | 10 | S | 1 |
| S. pneumoniae | R36A | | | 1 |
| S. pneumoniae | Lyt 4-4 | | | 1 |
| S. gordonii | PK 2565 | | | 2 |
| S. mitis | J 22 | | | 2 |
| S. mutans | OMZ 175 | | | 3 |
| S. oralis | H 1 | | | 2 |
| S. salivarius | ATCC 27945 | | | 2 |

Susceptibility to Penicillin: R, resistant; I, intermediate; S, susceptible.
Source:
1, Alexander Tomasz, The Rockefeller University, New York, NY;
2, Paul Kohlenbrander, National Institute of Dental and Craniofacial Research, Bethesda, MD;
3, Ivo Van de Rijn, Wake Forest University, Winston-Salem, NC.

Three highly penicillin-resistant strains were also included, which represent the internationally spread clones Sp9-3, Sp14-3 and Sp23-1, that account for a majority of penicillin-resistant pneumococci in day care centers and hospitals (R. Sa-Leao, et al., J Infect Dis 182, 1153-60. (2000), R. B. Roberts, A. Tomasz, A. Corso, J. Hargrave, E. Severina, Microb Drug Resist 7, 137-52. (2001), incorporated herein by reference). In 30 seconds, 100 U of Pal decreased the viable titer of the 15 strains of exponentially growing S. pneumoniae by Log10 4.0 cfu/ml (median, range 3.3-4.7) as compared to controls incubated with the enzyme buffer alone.

Figure 2:
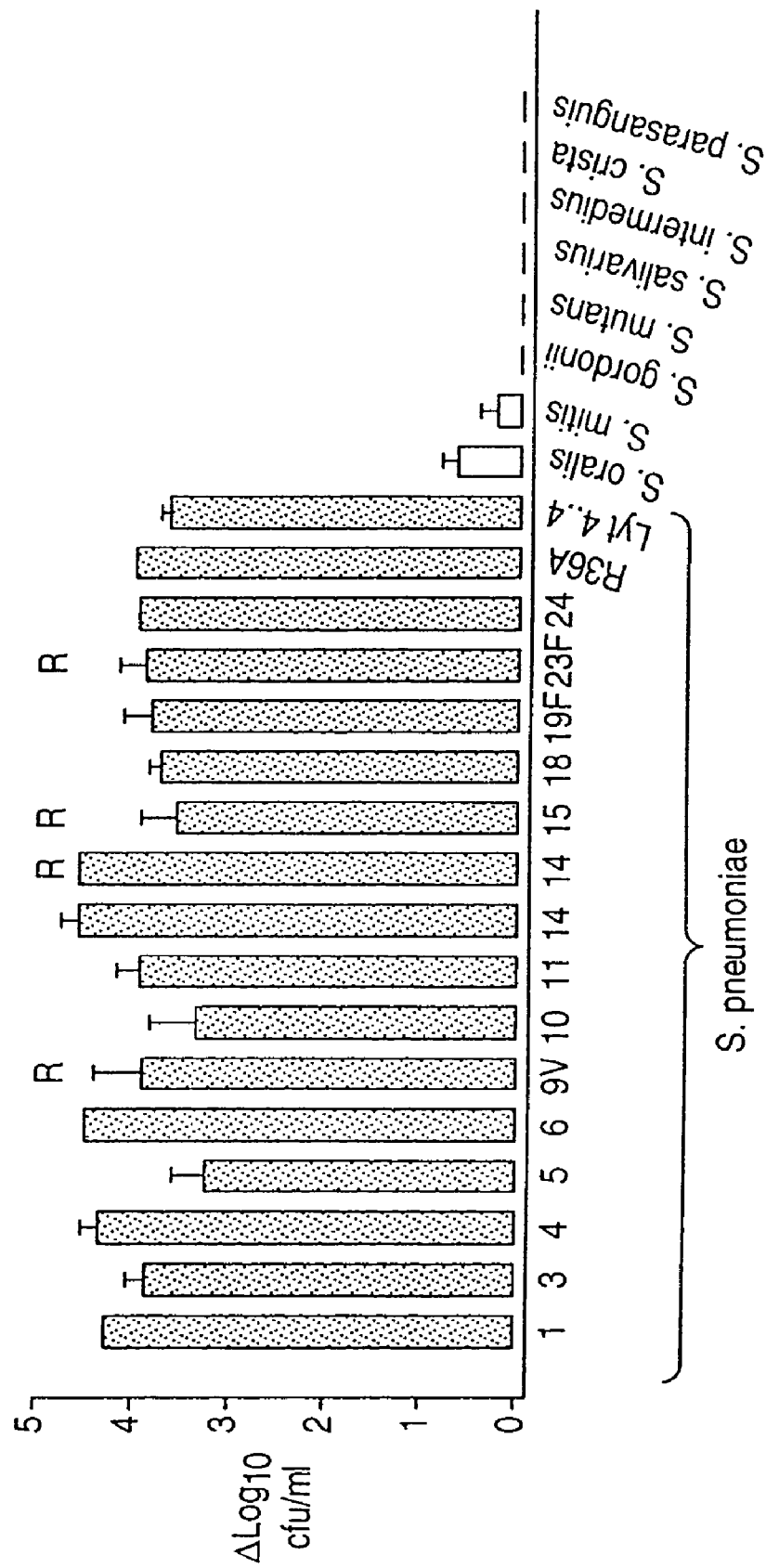
FIG. 2 is a graph showing the in vitro killing of 15 clinical *S. pneumoniae* strains, 2 pneumococcal mutants and 5 oral streptococcal species in log-phase with Pal.

FIG. 2 shows the in vitro killing of 15 clinical S. pneumoniae strains, 2 pneumococcal mutants and 5 oral streptococcal species in log-phase with 100 U/ml Pal during 30 seconds, expressed as the decrease of bacterial titers in powers of 10. Numbers above "S. pneumoniae" indicate serotypes; bold print designates the 9 most frequently isolated serogroups. The error bars show standard deviation of triplicates. I: intermediate susceptibility to penicillin (MIC 0.1-1.0), R: highly penicillin resistant (MIC$^3$ 2.0). Pneumococci with intermediate (n=1) and high penicillin resistance (n=3) were killed at the same rate as penicillin sensitive strains (median (range) Log10 4.0 (3.7-4.7) vs. Log10 4.1 (3.3-4.7) cfu/ml, p=NS). Moreover, the capsule-deficient laboratory strain R36A and the mutant Lyt 4-4, deficient in a capsule and lacking the major pneumococcal autolysin LytA, showed identical susceptibility to Pal as the clinical pneumococcal isolates (decrease of Log10 4.2 and 3.9 cfu/ml, respectively, p=NS). The latter results suggest that the pneumococcal capsule does not interfere with the enzyme's access to the cell wall and that autolysin does not contribute significantly to cell lysis caused by Pal. One hundred units of Pal also killed exponentially growing S. oralis and S. mitis, but at a significantly lower rate (Log10 0.8 and Log10 0.23 cfu/ml, respectively, p<0.05). Both strains are known to incorporate choline in their cell walls and therefore provide a binding site for the enzyme (S. H. Gillespie, et al. Infect Immun 61, 3076-7 (1993), incorporated by reference). The remaining oral streptococcal strains were unaffected with enzyme concentrations as high as 10,000 U/ml and up to 10 min of exposure.

In vitro, S. pneumoniae, including the R36A and Lyt 4-4 mutants, in stationary phase were more resistant to the lethal action of Pal. Nevertheless, exposure to 10,000 U/ml resulted in killing of Log10 3.0 cfu/ml (median, range 3.0-4.0) in 30 sec. The mechanism responsible for the decrease in susceptibility to hydrolysis by Pal in non-growing pneumococci is likely to be a change in the cell wall structure (E. I. Tuomanen, A. Tomasz, Scand J Infect Dis Suppl. 74, 102-12 (1991), incorporated herein by reference), such as an increase in peptidoglycan cross-linking.

Figure 3:
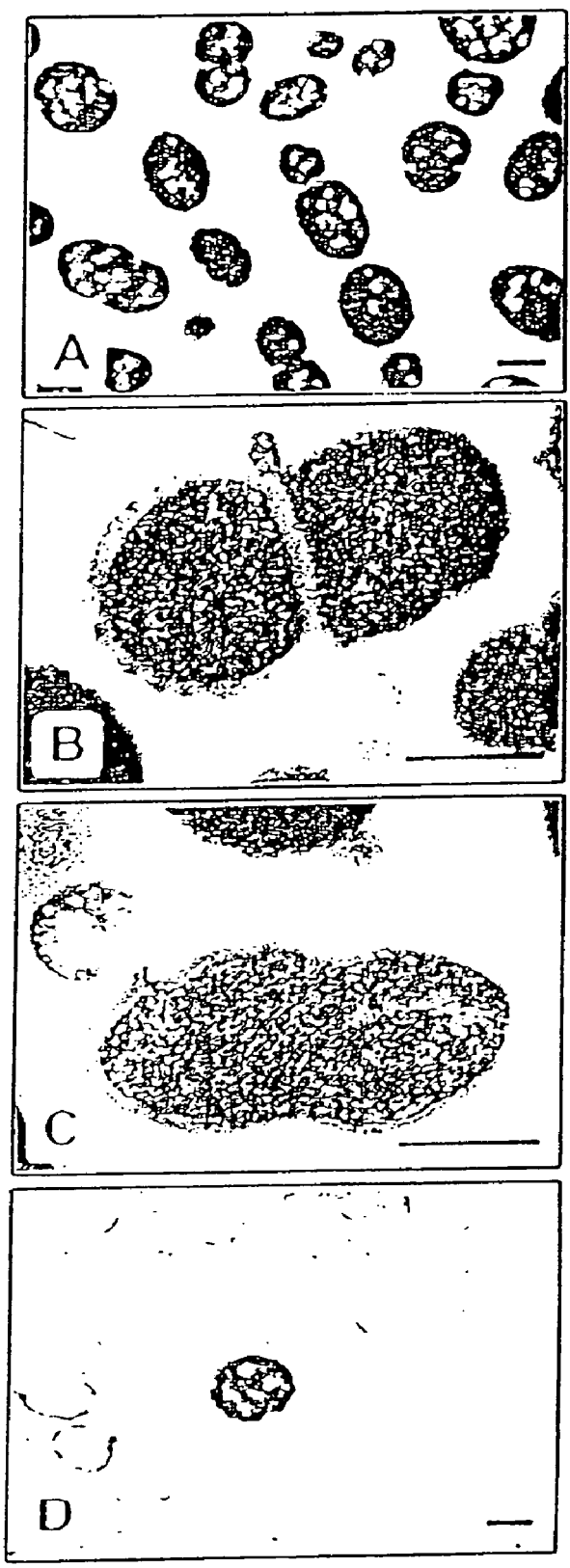
FIG. 3A, FIG. 3B, FIG. 3C and FIG. 3D are electron micrographs of cells of *S. pneumoniae* as they are exposed to Pal enzyme.

To study electron microscopy imaging, S. pneumoniae serogroup 14 was exposed to only 50 U/ml of Pal for 1 min. Specifically, S. pneumoniae strain DCC 1490 was grown in BHI to logarithmic phase, centrifuged and resuspended in sterile saline to an absorbance at 600 nm of 1.0. 500 ul of the suspension were incubated at room temperature with 500 ul of Pal at a final concentration of 50 U/ml. The lytic reaction was stopped after 10 sec, 1 min and 5 min by addition of glutaraldehyde (final concentration 2.5%). Bacteria and debris were pelleted by centrifugation and overlaid with 2.5% glutaraldehyde in 0.1 M cacodylate buffer (pH7.4). The samples were then postfixed in 1% osmium tetroxide, block stained with uranyl acetate and processed according to standard procedures by The Rockefeller University Electron Microscopy Service. Electron microscopy shown in FIG. 3 reveals protrusions of the cell membrane and the cytoplasm through single breaks in the cell wall, which appeared predominantly near the septum of the dividing diplococci (FIG. 3B). After 5 min, empty cell walls remained, retaining their original shape, indicating that digestion of amide bonds in a restricted location within the cell wall is sufficient for cell death (FIG. 3D). FIG. 3A shows the cell prior to exposure to the enzyme, and FIG. 3C shows the cell as it is dying.

The ability of Pal to eradicate S. pneumoniae from a mucosal surface was then tested in vivo in a mouse model of nasopharyngeal colonization following the model of H. Y. Wu, et al., Microb. Pathog. 23, 127-37 (1997), (incorporated by reference) with minor modifications. S. pneumoniae strain DCC 1490 was grown to logarithmic phase, centrifuged and resuspended to a predefined titer of 1010 cfu/ml. Swiss CD-1 mice (weight range 22 to 24 g, Charles River Laboratories, Wilmington, Mass.) were anesthetized with a mixture of ketamine (Fort Dodge Animal Health, Fort Dodge, Iowa, 1.2 mg/animal) and xylazine (Miles Inc., Shawnee Mission, Kans., 0.25 mg/animal), and inoculated in one nostril with 10 ul of the bacterial suspension (n=18) or 10 ul of sterile saline (n=3). Forty-two hours later, inoculated animals were again anesthetized and 25 ul of Pal (350 U, n=9) or enzyme buffer (n=9) was instilled in each nostril over several minutes. The mouth of each animal was rinsed with additional 50 ul Pal (700 U), for a total of 1400 U. Five hours later, all animals were euthanized and the nasal cavity was washed through the dissected trachea with 60 ul of sterile saline. The nasal wash was serially 10-fold diluted and plated on blood agar for titer determination. The following day, alpha-hemolytic colonies were respread on blood agar and incubated with an optochin disk (BBL, Sparks, Md.). Bacteria with a zone of inhibition greater than or equal to about 14 mm were believed to be S. pneumoniae. Groups were compared with the Mann-Whitney test.

Figure 4:
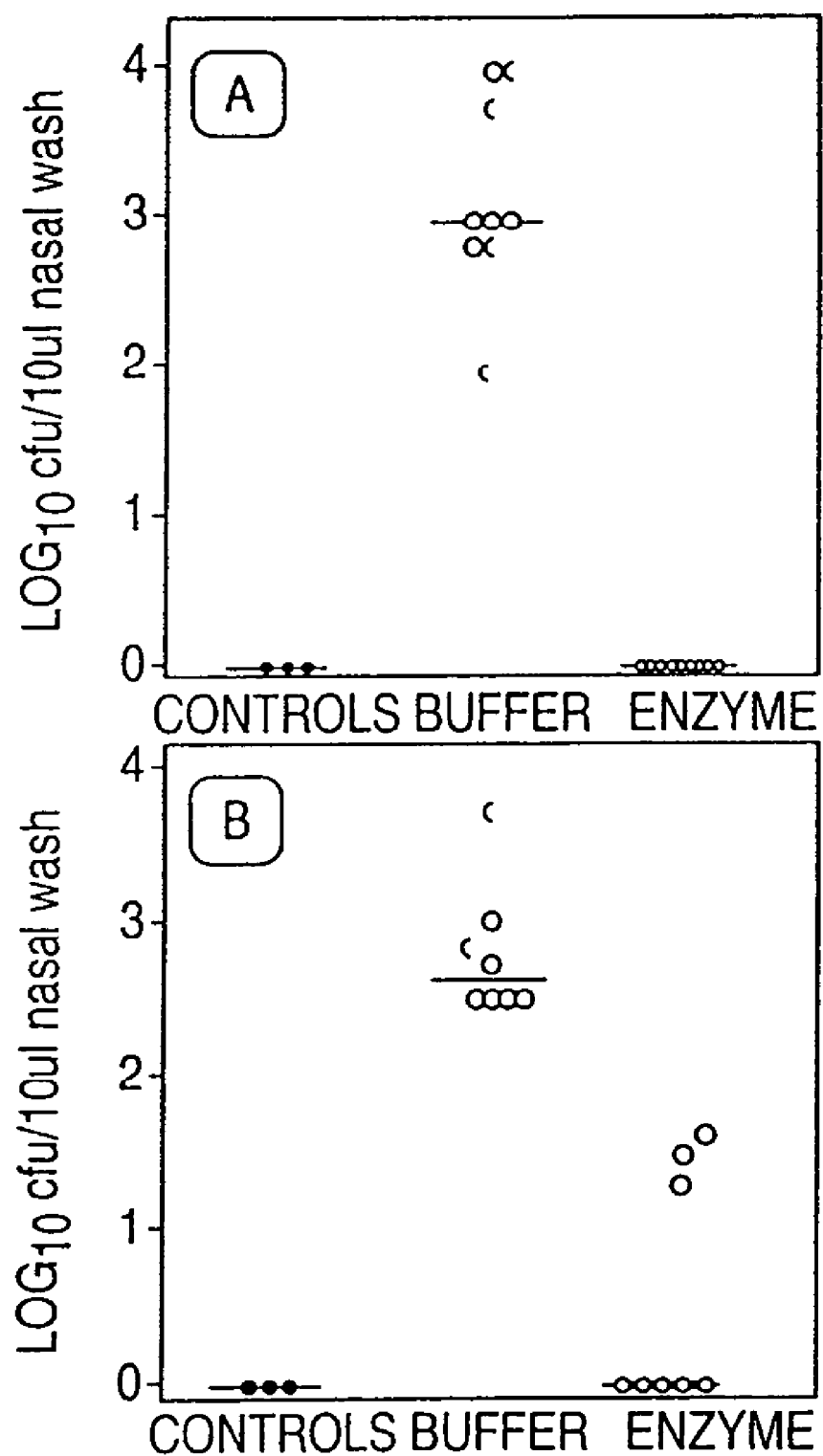
FIG. 4A and FIG. 4B are graphs showing the elimination of *S. pneumoniae* serotype 14 in the mouse model of nasopharyngeal carriage.

Treatment with Pal eliminated S. pneumoniae to undetectable levels (Log10 0 cfu/10 ul nasal wash) as opposed to treatment with buffer only (median [range] Log10 3.0 [2.0-3.0] cfu/10 ul, p<0.001) (FIG. 4A). The experiment was repeated with a lower dose of enzyme, randomizing the animals (n=16) for treatment with a total of 700 U of Pal or buffer. Enzyme treatment here completely eliminated pneumococci from 5 of 8 animals and significantly decreased titers in the remaining 3 (p<0.001) (FIG. 4B). Each experiment included 3 uncolonized control animals that revealed no S.

*pneumoniae*. These results indicate that pneumococci on mucosal surfaces are highly susceptible to the action of the lytic enzyme.

To determine if repeated exposure to low concentrations of Pal enzyme is able to select for enzyme-resistant *S. pneumoniae*, strain DCC 1490 was grown on blood agar plates and exposed to low concentrations of Pal (<1 U). Colonies at the periphery of a clearing zone were picked, grown to logarithmic phase, streaked on a fresh plate and re-exposed to Pal. Sixteen rounds of exposure did not result in decrease of susceptibility to Pal when compared to the unexposed strain using the in vitro killing assay (p=NS (nonsignificant)), suggesting that resistance to Pal may occur at a very low frequency. It has been shown that the cell wall receptor for Pal as well as other pneumococcal phage lytic enzymes is choline, a molecule that is necessary for pneumococcal viability (R. Lopez, E. Garcia, P. Garcia, J. L. Garcia, Microb Drug Resist 3, 199-211. (1997), A. Tomasz, Science 157, 694-7. (1967), incorporated herein by reference).

Observation of colonization status after a single treatment with Pal 1400 U/ml vs. buffer (FIG. 7) was also performed. Buffer-treated mice remained colonized throughout the duration of the experiment, with titers decreasing from day 6. In animals treated with Pal enzyme, *S. pneumoniae* reappeared discretely from day 2. However, titers did not reach a level necessary for successful recolonization in this model (p<0.0001 for the comparison of both curves). One control animal was tested on days 0, 4, and 8.

The action of phage lytic enzymes is believed to be specific for a structure found in the bacterial peptidoglycan, and such structures are not believed to be present in mammalian tissues, one skilled in the art would expect that its effect on the human mucous membrane will be minimal or nonexistent. Also, no immune response is expected from nasal treatment with micrograms of Pal, since co-administration of higher protein concentrations with a mucosal adjuvant is generally necessary to elicit efficient mucosal immunity (L. Haan, et al., Vaccine 19, 2808-907 (2001). Similarly, altered lytic enzymes will most likely not elicit an immune response.

In all of the above phage associated lytic enzymes, the lytic enzyme may be coded for by the sequences of phage Dp-1 (see SEQ. 1 and SEQ 2) or they may be coded for by the DNA of other phages for lytic enzymes are specific for *Streptococcus pneumoniae*.

A large variety of isolated cDNA sequences that encode lytic enzymes and partial sequences that hybridize with such gene sequences are useful for recombinant production of the lytic enzyme. Representative nucleic acid sequences in this context are SEQ ID No. 2 sequence shown in FIG. 6 and sequences that hybridize with complementary sequences of a DNA having a sequence shown in FIG. 6 under stringent conditions. Bases 3687 to 4577 of SEQ. ID No. 2 genetically code for the Pal lytic enzyme. Still further variants of these sequences and sequences of nucleic acids that hybridize with those shown in the figures also are contemplated for use in production of lysing enzymes according to the invention, including natural variants that may be obtained.

Polynucleotide sequences comprising one or more small DNA molecules derived from the disclosed DNA molecules are also provided by this application. Such small DNA molecules include oligonucleotides suitable for use as hybridization probes or polymerase chain reaction (PCR) primers. As such, these small DNA molecules will comprise at least a segment of a lytic enzyme genetically coded for by a bacteriophage specific for *Streptococcus pneumoniae* and, for the purposes of PCR, will comprise at least a 10-15 nucleotide sequence and, more preferably, a 15-30 nucleotide sequence of the gene. DNA molecules and nucleotide sequences which are derived from the disclosed DNA molecules as described above may also be defined as DNA sequences which hybridize under stringent conditions to the DNA sequences disclosed, or fragments thereof.

Hybridization conditions corresponding to particular degrees of stringency vary depending upon the nature of the hybridization method of choice and the composition and length of the hybridizing DNA used. Generally, the temperature of hybridization and the ionic strength (especially the sodium ion concentration) of the hybridization buffer will determine the stringency of hybridization. Calculations regarding hybridization conditions required for attaining particular degrees of stringency are discussed by Sambrook et al. (1989), In Molecular Cloning: A Laboratory Manual, Cold Spring Harbor, N.Y., chapters 9 and 11 (incorporated by reference in its entirety).

A hybridization experiment may be performed by hybridization of a DNA molecule (for example, a natural variation of the lytic enzyme genetically coded for by a bacteriophage specific for *Streptococcus pneumoniae*) to a target DNA molecule. A target DNA may be, for example, the corresponding cDNA which has been electrophoresed in an agarose gel and transferred to a nitrocellulose membrane by Southern blotting (Southern (1975). J. Mol. Biol. 98:503), a technique well known in the art and described in Sambrook et al. (1989) In Molecular Cloning: A Laboratory Manual, Cold Spring Harbor, N.Y. (incorporated herein by reference). Hybridization with a target probe labeled with isotopic P (32) labeled-dCTP is carried out in a solution of high ionic strength such as 6 times SSC at a temperature that is 20-25 degrees Celsius below the melting temperature, Tm, (described infra). For such Southern hybridization experiments where the target DNA molecule on the Southern blot contains 10 ng of DNA or more, hybridization is carried out for 6-8 hours using 1-2 ng/ml radiolabeled probe (of specific activity equal to 109 CPM/mug or greater). Following hybridization, the nitrocellulose filter is washed to remove background hybridization. The washing conditions are as stringent as possible to remove background hybridization while retaining a specific hybridization signal. The term "Tm" represents the temperature above which, under the prevailing ionic conditions, the radiolabeled probe molecule will not hybridize to its target DNA molecule.

The $T_m$ of such a hybrid molecule may be estimated from the following equation: Tm=81.5 degrees C.−16.6(log10 of sodium ion concentration)+0.41 (% G+C)−0.63(% formamide)−(600/l) where l=the length of the hybrid in base pairs. This equation is valid for concentrations of sodium ion in the range of 0.01M to 0.4M, and it is less accurate for calculations of Tm in solutions of higher sodium ion concentration (Bolton and McCarthy (1962). Proc. Natl. Acad. Sci. USA 48:1390) (incorporated herein by reference). The equation also is valid for DNA having G+C contents within 30% to 75%, and also applies to hybrids greater than 100 nucleotides in length. The behavior of oligonucleotide probes is described in detail in Ch. 11 of Sambrook et al. (1989). In Molecular Cloning: A Laboratory Manual, Cold Spring Harbor, N.Y. (incorporated herein by reference). The preferred exemplified conditions described here are particularly contemplated for use in selecting variations of the lytic gene.

Thus, by way of example, of a 150 base pair DNA probe derived from the first 150 base pairs of the open reading frame of a cDNA having a % GC=45%, a calculation of hybridization conditions required to give particular stringencies may be made as follows:

Assuming that the filter will be washed in 0.3×SSC solution following hybridization, sodium ion=0.045M;% GC=45%; Formamide concentration=0 1=150 base pairs (see equation in Sambrook et al.) and so Tm=74.4 degrees C. The Tm of double-stranded DNA decreases by 1-1.5 degrees C. with every 1% decrease in homology (Bonner et al. (1973). J. Mol. Biol. 81:123). Therefore, for this given example, washing the filter in 0.3 times SSC at 59.4-64.4 degrees C. will produce a stringency of hybridization equivalent to 90%; DNA molecules with more than 10% sequence variation relative to the target BSMR cDNA will not hybridize. Alternatively, washing the hybridized filter in 0.3 times SSC at a temperature of 65.4-68.4 degrees C. will yield a hybridization stringency of 94%; DNA molecules with more than 6% sequence variation relative to the target BSMR cDNA molecule will not hybridize. The above example is given entirely by way of theoretical illustration. One skilled in the art will appreciate that other hybridization techniques may be utilized and that variations in experimental conditions will necessitate alternative calculations for stringency.

In preferred embodiments of this application, stringent conditions may be defined as those under which DNA molecules with more than 25% sequence variation (also termed "mismatch") will not hybridize. In a more preferred embodiment, stringent conditions are those under which DNA molecules with more than 15% mismatch will not hybridize, and more preferably still, stringent conditions are those under which DNA sequences with more than 10% mismatch will not hybridize. In a most preferred embodiment, stringent conditions are those under which DNA sequences with more than 6% mismatch will not hybridize.

The degeneracy of the genetic code further widens the scope of this application as it enables major variations in the nucleotide sequence of a DNA molecule while maintaining the amino acid sequence of the encoded protein. For example, a representative amino acid residue is alanine. This may be encoded in the cDNA by the nucleotide codon triplet GCT. Because of the degeneracy of the genetic code, three other nucleotide codon triplets—GCT, GCC and GCA—also code for alanine. Thus, the nucleotide sequence of the gene could be changed at this position to any of these three codons without affecting the amino acid composition of the encoded protein or the characteristics of the protein. The genetic code and variations in nucleotide codons for particular amino acids are well known to the skilled artisan. Based upon the degeneracy of the genetic code, variant DNA molecules may be derived from the cDNA molecules disclosed herein using standard DNA mutagenesis techniques as described above, or by synthesis of DNA sequences. DNA sequences which do not hybridize under stringent conditions to the cDNA sequences disclosed by virtue of sequence variation based on the degeneracy of the genetic code are herein comprehended by this invention.

One skilled in the art will recognize that the DNA mutagenesis techniques described here can produce a wide variety of DNA molecules that code for a bacteriophage lysin specific for *Streptococcus pneumoniae* yet that maintain the essential characteristics of the lytic protein. Newly derived proteins may also be selected in order to obtain variations on the characteristic of the lytic protein, as will be more fully described below. Such derivatives include those with variations in amino acid sequence including minor deletions, additions and substitutions. Many of the contemplated variant DNA molecules include those created by standard DNA mutagenesis techniques, for example, M13 primer mutagenesis. Details of these techniques are provided in Sambrook et al. (1989) In Molecular Cloning: A Laboratory Manual, Cold Spring Harbor, N.Y. (incorporated herein by reference). By the use of such techniques, variants may be created which differ in minor ways from those disclosed. DNA molecules and nucleotide sequences which are derivatives of those specifically disclosed herein and which differ from those disclosed by the deletion, addition or substitution of nucleotides while still encoding a protein which possesses the functional characteristic of the BSMR protein are contemplated by this invention.

Having provided nucleotide sequences that code for lytic enzyme genetically coded for by a bacteriophage specific for *Streptococcus pneumoniae* and fragments of that enzyme, correspondingly provided are the complementary DNA strands of the cDNA molecule and DNA molecules which hybridize under stringent conditions to the lytic enzyme cDNA molecule or its complementary strand. Such hybridizing molecules include DNA molecules differing only by minor sequence changes, including nucleotide substitutions, deletions and additions. Also contemplated are isolated oligonucleotides comprising at least a segment of the cDNA molecule or its complementary strand, such as oligonucleotides which may be employed as effective DNA hybridization probes or primers useful in the polymerase chain reaction. Hybridizing DNA molecules and variants on the lytic enzyme cDNA may readily be created by standard molecular biology techniques.

The detection of specific DNA mutations may be achieved by methods such as hybridization using specific oligonucleotides (Wallace et al. (1986). Cold Spring Harbor Symp. Quant. Biol. 51:257-261), direct DNA sequencing (Church and Gilbert (1988). Proc. Natl. Acad. Sci. USA 81:1991-1995), the use of restriction enzymes (Flavell et al. (1978). Cell 15:25), discrimination on the basis of electrophoretic mobility in gels with denaturing reagent (Myers and Maniatis (1986). Cold Spring Harbor Symp. Quant. Biol. 51:275-284), RNase protection (Myers et al. (1985). Science 230:1242), chemical cleavage (Cotton et al. (1985). Proc. Natl. Acad. Sci. USA 85:4397-4401) (incorporated herein by reference), and the ligase-mediated detection procedure (Landegren et al., 1988).

Oligonucleotides specific to normal or mutant sequences can be chemically synthesized using commercially available machines, labeled radioactively with isotopes (such as .sup.32 P) or non-radioactively (with tags such as biotin (Ward and Langer et al. Proc. Natl. Acad. Sci. USA 78:6633-6657 1981) (incorporated herein by reference), and hybridized to individual DNA samples immobilized on membranes or other solid supports by dot-blot or transfer from gels after electrophoresis. The presence or absence of these specific sequences are visualized by methods such as autoradiography or fluorometric or colorimetric reactions (Gebeyehu et al. Nucleic Acids Res. 15:4513-4534 1987) (incorporated herein by reference).

Sequence differences between normal and mutant forms of the gene may also be revealed by the direct DNA sequencing method of Church and Gilbert (1988) (incorporated herein by reference). Cloned DNA segments may be used as probes to detect specific DNA segments. The sensitivity of this method is greatly enhanced when combined with PCR (Stoflet et al. Science 239:491-494, 1988) (incorporated herein by reference). In this approach, a sequencing primer which lies within the amplified sequence is used with double-stranded PCR product or single-stranded template generated by an altered PCR. The sequence determination is performed by conventional procedures with radiolabeled nucleotides or by automatic sequencing procedures with fluorescent tags. Such sequences are useful for production of lytic enzymes.

For example, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to a protein of interest using a sequence which facilitates purification, such as with a GST domain.

By way of another example, a signal sequence of this application can be used to identify regulatory sequences, i.e., promoters, enhancers, repressors. Since signal sequences are the most amino-terminal sequences of a peptide, it is expected that the nucleic acids which flank the signal sequence on its amino-terminal side will be regulatory sequences that affect transcription. Thus, a nucleotide sequence which encodes all or a portion of a signal sequence can be used as a probe to identify and isolate the signal sequence and its flanking region, and this flanking region can be studied to identify regulatory elements therein.

The lytic enzyme can be genetically coded for by a bacteriophage specific for *Streptococcus pneumoniae* having a particular amino acid sequence identity including a sequence selected from the group consisting of: SEQ ID No. 1, a variant sequence lytic enzyme of SEQ ID No. 1 with one or more chemical alterations including amino acid additions, substitutions or deletions, and variants or combinations thereof, including altered polypeptide sequences of these polypeptides.

A lytic enzyme can be encoded by any corresponding polypeptide. The lytic enzyme may be encoded by a polypeptide corresponding to a functionally active lytic enzyme. For example, the lytic enzyme is encoded by a variant of SEQ ID No. 1. Sequence variants of a lytic enzyme coding polypeptide sequence have an altered amino acid sequence which can function as either agonists (mimetics) or as antagonists. Variants can be generated by mutagenesis, i.e., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

The altered form of the protein or peptides and peptide fragments, as disclosed herein, includes, protein or peptides and peptide fragments that are chemically synthesized or prepared by recombinant DNA techniques, or both. These techniques include, for example, chimerization and shuffling. When the protein or peptide is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Variants of a protein which function as either agonists (mimetics) or as antagonists can be identified by screening combinatorial libraries of mutants, i.e., truncation mutants, of the protein for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (i.e., for phage display). There are a variety of methods which can be used to produce libraries of potential variants of the polypeptides from a degenerate oligonucleotide sequence. Methods for synthesizing degenerate oligonucleotides are known in the art (see, i.e., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477, all herein incorporated by reference).

Amino acid substitutions are typically of single residues; insertions usually will be on the order of about from 1 to 10 amino acid residues; and deletions will range about from 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. Obviously, the mutations that are made in the DNA encoding the protein must not place the sequence out of reading frame and preferably will not create complementary regions that could produce secondary mRNA structure (EP 75,444A).

Substitutional variants are those in which at least one residue in the amino acid sequence has been removed and a different residue inserted in its place. Such substitutions generally are made in accordance with the following Table 1 when it is desired to finely modulate the characteristics of the protein. Table 1 shows amino acids which may be substituted for an original amino acid in a protein and which are regarded as conservative substitutions.

TABLE 2

Examples of Conservative Amino Acid Substitutions
Original Residue/Conservative Substitutions

| | |
|---|---|
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than in Table 2, i.e., selecting residues that differ more significantly in their effect on maintaining: (a) the structure of the polypeptide backbone in the area of the substitution, for example, as a sheet or helical conformation; (b) the charge or hydrophobicity of the molecule at the target site; or (c) the bulk of the side chain. The substitutions which in general are expected to produce the greatest changes in protein properties will be those in which: (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The effects of these amino acid substitutions or deletions or additions may be assessed for derivatives of the lytic enzyme protein by analyzing the ability of the derivative proteins to complement the sensitivity to DNA cross-linking agents exhibited by phages in infected bacteria hosts. These assays may be performed by transfecting DNA molecules encoding the derivative proteins into the bacteria as described above.

While the site for introducing an amino acid sequence variation can be predetermined, the mutation per se does not need to be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known.

There are a number of bacteriophages for *S. pneumoniae*, including but not limited to Dp-1, DP-4, Cp-1, Cp-7, Cp-9, Cp-5, MM1, EJ-1, HB-3, HB-623, HB-746, ω-1, and ω-2. The pneumococcal phages from which the gene for the lytic enzyme is cloned are classified in four groups based on their viral families. All contain double-stranded DNA and a cell wall lytic system consisting of a holin that permeabilizes the cell membrane, and either an N-acetylmuramoyl-L-alanine amidase (amidase) or a lysozyme, capable of digesting the pneumococcal cell wall. (P. Garcia, A. C. Martin, R. Lopez, Microb Drug Resist 3, 165-76 (1997), incorporated by reference). Both types of enzymes contain a C-terminal choline-binding domain common to many pneumococcal proteins and an N-terminal catalytic domain. The lytic system allows the virus to escape the host cell after successful replication.

While some preferred embodiments use a Dp 1 phage was to produce Pal which specifically kills *Streptococcus pneumoniae*, other phages may be used to produce an enzyme specific for *Streptococcus pneumoniae*.

As used herein, shuffled proteins or peptides are molecules in which the genes, gene products, or peptides for more than one related phage protein or protein peptide fragments have been randomly cleaved and reassembled into a more active or specific protein. Shuffled oligonucleotides, peptides or peptide fragment molecules are selected or screened to identify a molecule having a desired functional property. This method is described, for example, in Stemmer, U.S. Pat. No. 6,132,970 (Method of shuffling polynucleotides); Kauffman, U.S. Pat. No. 5,976,862 (Evolution via Condon-based Synthesis) and Huse, U.S. Pat. No. 5,808,022 (Direct Codon Synthesis). The contents of these patents are incorporated herein by reference.

Shuffling is used to create a protein that is 10 to 100 fold more active than the template protein. The template protein is selected among different varieties of lysin or holin proteins. The shuffled protein or peptides constitute, for example, one or more binding domains and one or more catalytic domains. Each binding or catalytic domain is derived from the same or a different phage or phage protein. The shuffled domains are either oligonucleotide based molecules, as gene or gene products, that either alone or in combination with other genes or gene products are translatable into a peptide fragment, or they are peptide based molecules. Gene fragments include any molecules of DNA, RNA, DNA-RNA hybrid, antisense RNA, Ribozymes, ESTs, SNIPs and other oligonucleotide-based molecules that either alone or in combination with other molecules produce an oligonucleotide molecule capable or incapable of translation into a peptide.

In addition, libraries of fragments of the coding sequence of a polypeptide can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein (Arkin and Yourvan (1992) Proc. Natl. Acad. Sci. USA 89:7811-7815; Delgrave et al. (1993) Protein Engineering 6(3):327-331).

Biologically active portions of a protein or peptide fragment, as described herein, include polypeptides comprising amino acid sequences sufficiently identical to or derived from the amino acid sequence of the phage protein, which include fewer amino acids than the full length protein of the phage protein and exhibit at least one activity of the corresponding full-length protein. Typically, biologically active portions comprise a domain or motif with at least one activity of the corresponding protein. A biologically active portion of a protein or protein fragment can be a polypeptide which is, for example, 10, 25, 50, 100 less or more amino acids in length. Moreover, other biologically active portions, in which other regions of the protein are deleted, or added can be prepared by recombinant techniques and evaluated for one or more of the functional activities of the native form of a polypeptide.

A signal sequence of a polypeptide can facilitate transmembrane movement of the protein and peptides and peptide fragments to and from mucous membranes, as well as by facilitating secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, polypeptides having a signal sequence are provided, as well as to the signal sequence itself and to the polypeptide in the absence of the signal sequence (i.e., the cleavage products).

A "chimeric protein" or "fusion protein" comprises all or (preferably a biologically active) part of a polypeptide operably linked to a heterologous polypeptide. The term "operably linked" when referring to a first polypeptide and a second heterologous polypeptide, indicates that the two polypeptides are fused in-frame. The heterologous polypeptide can be fused to the N-terminus or C-terminus of the polypeptide. Chimeric proteins are produced enzymatically by chemical synthesis, or by recombinant DNA technology.

Chimeric proteins or peptides are produced, for example, by combining two or more proteins having two or more active sites. Chimeric protein and peptides can act independently on the same or different molecules, and hence have a potential to treat two or more different bacterial infections at the same time. Chimeric proteins and peptides also are used to treat a bacterial infection by cleaving the cell wall in more than one location.

A number of chimeric lytic enzymes have been produced and studied. Gene E-L, a chimeric lysis constructed from bacteriophages phi X174 and MS2 lysis proteins E and L, respectively, was subjected to internal deletions to create a series of new E-L clones with altered lysis or killing properties. The lytic activities of the parental genes E, L, E-L, and the internal truncated forms of E-L were investigated in this study to characterize the different lysis mechanism, based on differences in the architecture of the different membranes spanning domains. Electron microscopy and release of marker enzymes for the cytoplasmic and periplasmic spaces revealed that two different lysis mechanisms can be distinguished depending on penetration of the proteins of either the inner membrane or the inner and outer membranes of the *E. coli*. FEMS Microbiol. Lett. 1998 July 1, 164(1); 159-67 (incorporated herein by reference).

In another experiment an active chimeric cell wall lytic enzyme (TSL) was constructed by fusing the region coding for the N-terminal half of the lactococcal phage Tuc2009 lysin and the region coding for the C-terminal domain of the major pneumococcal autolysin. The chimeric enzyme exhibited a glycosidase activity capable of hydrolysing choline-containing pneumococcal cell walls.

One useful fusion protein is a GST fusion protein in which the polypeptide is fused to the C-terminus of a GST sequence. Such chimeric protein can facilitate the purification of a recombinant polypeptide.

The chimeric protein or peptide may contain a heterologous signal sequence at its N-terminus. For example, the native signal sequence of a polypeptide can be removed and replaced with a signal sequence from another protein. For example, the gp67 secretory sequence of the baculovirus envelope protein can be used as a heterologous signal sequence (Current Protocols in Molecular Biology, Ausubel et al., eds., John Wiley & Sons, 1992, incorporated herein by reference). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

The fusion protein may be an immunoglobulin fusion protein in which all or part of a polypeptide is fused to sequences derived from a member of the immunoglobulin protein family. An immunoglobulin fusion protein can be incorporated into a pharmaceutical composition and administered to a subject to inhibit an interaction between a ligand (soluble or membrane-bound) and a protein on the surface of a cell (receptor), to thereby suppress signal transduction in vivo. The immunoglobulin fusion protein can alter bioavailability of a cognate ligand of a polypeptide. Inhibition of ligand/receptor interaction may be useful therapeutically, both for treating bacterial-associated diseases and disorders for modulating (i.e. promoting or inhibiting) cell survival. Moreover, an immunoglobulin fusion protein can be used as an immunogen to produce antibodies directed against a polypeptide in a subject, to purify ligands and in screening assays to identify molecules which inhibit the interaction of receptors with ligands. The pharmaceutical composition may also contain antibodies directed against a phage protein or peptide fragment of the invention.

Chimeric and fusion proteins and peptides can be produced by standard recombinant DNA techniques. For example, the fusion gene can be synthesized by conventional techniques, including automated DNA synthesizers. Alternatively, PCR amplification of gene fragments can be carried out using anchor primers which give rise to complementary overhangs between two consecutive gene fragments which subsequently can be annealed and reamplified to generate a chimeric gene sequence (see, i.e., Ausubel et al., supra). Moreover, many expression vectors are commercially available that already encode a fusion moiety (i.e., a GST polypeptide). A nucleic acid encoding a polypeptide can be cloned into such an expression vector such that the fusion moiety is linked in-frame to the polypeptide with at least one holin protein, which may also be chimeric, shuffled, or "natural."

The therapeutic composition may also comprise a holin protein. Holin proteins (or "holins") are proteins which produce holes in the cell membrane. Holin proteins may form lethal membrane lesions that terminate cellular respiration in a bacteria. Like the lytic proteins, holin proteins are coded for and carried by a phage. In fact, it is quite common for the genetic code of the holin protein to be next to or even within the code for the phage lytic protein. Most holin protein sequences are short, and overall, hydrophobic in nature, with a highly hydrophilic carboxy-terminal domain. In many cases, the putative holin protein is encoded on a different reading frame within the enzymatically active domain of the phage. In other cases, holin protein is encoded on the DNA next or close to the DNA coding for the cell wall lytic protein. Holin proteins are frequently synthesized during the late stage of phage infection and found in the cytoplasmic membrane where they cause membrane lesions.

Holins can be grouped into two general classes based on primary structure analysis. Class I holins are usually 95 residues or longer and may have three potential transmembrane domains. Class II holins are usually smaller, at approximately 65-95 residues, with the distribution of charged and hydrophobic residues indicating two TM domains (Young, et al. Trends in Microbiology v. 8, No. 4, March 2000). At least for the phages of gram-positive hosts, however, the dual-component lysis system may not be universal. Although the presence of holins has been shown or suggested for several phages, no genes have yet been found encoding putative holins for all phages. Holins have been shown to be present in several bacteria, including, for example, lactococcal bacteriophage Tuc2009, lactococcal NLC3, pneumococcal bacteriophage EJ-1, *Lactobacillus gasseri* bacteriophage Nadh, *Staphylococcus aureus* bacteriophage Twort, *Listeria monocytogenes* bacteriophages, pneumococcal phage Cp-1, *Bacillus subtillis* phage M29, *Lactobacillus delbrueckki* bacteriophage LL-H lysin, and bacteriophage N 11 of *Staphyloccous aureus*. (Loessner, et al., Journal of Bacteriology, August 1999, p. 4452-4460).

For example, holin proteins can be used in conjunction with the lytic enzymes to accelerate the speed and efficiency at which the bacteria are killed. Holin proteins may also be in the form of chimeric and/or shuffled enzymes. Holin proteins may also be used alone in the treatment of bacterial infections according to some embodiments.

A lytic enzyme may be produced by the bacterial organism after being infected with a particular bacteriophage as either a prophylactic treatment for preventing those who have been exposed to others who have the symptoms of an infection from getting sick, or as a therapeutic treatment for those who have already become ill from the infection. This application is based upon the discovery that phage lytic enzymes specific for bacteria infected with a specific phage can effectively and efficiently break down the cell wall of the bacterium in question. At the same time, the semipurified enzyme preferably lacks proteolytic enzymatic activity and is therefore nondestructive to mammalian proteins and tissues when present during the digestion of the bacterial cell wall. The lytic enzymes may be chimeric, shuffled or "natural," and may be in combination. Relevant U.S. Pat. No. 5,604,109 is incorporated herein in its entirety by reference.

While an enzyme can be produced by directly infecting *S. pneumoniae* with a Dp1 phage or another phage which is specific for a *S. pneumoniae*, the lytic enzyme may be also be produced by removing a gene for the lytic enzyme from the phage genome, putting the gene into a transfer vector, and cloning said transfer vector into an expression system.

An "altered" lytic enzyme can be produced in a number of ways. In a preferred embodiment, a gene for the altered lytic enzyme from the phage genome is put into a transfer or movable vector, preferably a plasmid, and the plasmid is cloned into an expression vector or expression system. The expression vector may be *E. coli, Bacillus*, or a number of other suitable bacteria. The vector system may also be a cell free expression system. All of these methods of expressing a gene or set of genes are known in the art. The lytic enzyme may also be created by infecting *Streptococcus pneumoniae* with a bacteriophage specific for *Streptococcus pneumoniae*, wherein said at least one lytic enzyme exclusively lyses the cell wall of said *Streptococcus pneumoniae* having at most minimal effects on other bacterial flora present.

Therapeutic pharmaceutical compositions comprising lytic enzymes are also provided, as well as related methods of use and methods of manufacture. Therapeutic pharmaceutical compositions may comprise one or more lytic enzymes, and optionally include natural, chimeric or shuffled lytic enzymes, optionally combined with other components such as a carrier, vehicle, polypeptide, polynucleotide, holin protein(s), one or more antibiotics or suitable excipients.

The enzymes included in the therapeutic compositions may be all or any combination of unaltered phage associated lytic enzyme(s), and chimeric and/or shuffled lytic enzymes. Additionally, different lytic enzymes genetically coded for by different phage for treatment of the same bacteria may be used. These lytic enzymes may also be any combination of "unaltered" lytic enzymes, and chimeric and shuffled lytic enzymes. The lytic enzyme(s) in a therapeutic composition for *Streptococcus pneumoniae* may be used alone or in combination with antibiotics or, if there are other invasive bacterial organisms to be treated, in combination with other phage associated lytic enzymes specific for other bacteria being targeted. The lytic enzyme, chimeric enzyme, and/or shuffled lytic enzyme may all be used in conjunction with a holin protein. The amount of the holin protein may also be varied. Various antibiotics may be optionally included in the therapeutic agent with the enzyme and with or without the presence of lysostaphin. More than one chimeric and/or shuffled lytic enzyme may also be included in the therapeutic agent.

The pharmaceutical composition can also include one or more altered lytic enzymes, including isozymes, analogs, or variants thereof, produced by chemical synthesis or DNA recombinant techniques. In particular, altered lytic protein can be produced by chimerization, shuffling, or both. The pharmaceutical composition may contain a combination of one or more natural lytic protein and one or more chimeric or shuffled lytic protein. The pharmaceutical composition may also contain a peptide or a peptide fragment of at least one lytic protein derived from the same or different bacteria species, with an optional addition of one or more complementary agent, and a pharmaceutically acceptable carrier.

The pharmaceutical composition can contain a complementary agent, including one or more conventional antibiotics. In order to accelerate treatment of the infection, the therapeutic agent may further include at least one complementary agent which can also potentiate the bactericidal activity of the lytic enzyme. The complementary agent can be erythromycin, clarithromycin, azithromycin, roxithromycin, other members of the macrolide family, penicilins, cephalosporins, and any combinations thereof in amounts which are effective to synergistically enhance the therapeutic effect of the lytic enzyme. Virtually any other antibiotic may be used with the altered and/or unaltered lytic enzyme. Similarly, other lytic enzymes may be included in the carrier to treat other bacterial infections. Holin proteins may be included in the therapeutic treatment. Antibiotic supplements may be used in virtually all uses of the enzyme when treating different diseases. The pharmaceutical composition can also contain a peptide or a peptide fragment of at least one holin protein, or at least one holin and one lytic protein, which lytic and holin proteins are each derived from the same or different bacteria species, with an optional addition of a complementary agents, and a suitable carrier or diluent.

Also provided are compositions containing nucleic acid molecules that either alone or in combination with other nucleic acid molecules are capable of expressing an effective amount of lytic and/or holin proteins or a peptide fragment of the lytic and/or holin proteins in vivo. Cell cultures containing these nucleic acid molecules polynucleotides and vectors carrying and expressing these molecules in vitro or in vivo are also provided.

Therapeutic compositions may comprise lytic enzymes combined with a variety of carriers to treat the illnesses caused by *S. pneumoniae*. A carrier may have comprise than one shuffled and/or chimeric lytic enzyme. For instance, a carrier may comprise just a shuffled and/or chimeric lytic enzyme or it may also include the lytic enzymes for, example, *Haemophilus influenzae*. All compositions containing uses for shuffled or chimeric enzymes may contain unaltered lytic enzymes and holin proteins.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts, e.g., NaCl, KCl, $MgCl_2$, $CaCl_2$, and others.

Glycerin or glycerol (1,2,3-propanetriol) is commercially available for pharmaceutical use. It may be diluted in sterile water for injection, or sodium chloride injection, or other pharmaceutically acceptable aqueous injection fluid, and used in concentrations of 0.1 to 100% (v/v), preferably 1.0 to 50% more preferably about 20%.

DMSO is an aprotic solvent with a remarkable ability to enhance penetration of many locally applied drugs. DMSO may be diluted in sterile water for injection, or sodium chloride injection, or other pharmaceutically acceptable aqueous injection fluid, and used in concentrations of 0.1 to 100% (v/v). The carrier vehicle may also include Ringer's solution, a buffered solution, and dextrose solution, particularly when an intravenous solution is prepared.

Any of the carriers for the lytic enzyme may be manufactured by conventional means. However, it is preferred that any mouthwash or similar type products not contain alcohol to prevent denaturing of the enzyme. Similarly, when the lytic enzyme(s) is being placed in a cough drop, gum, candy or lozenge during the manufacturing process, such placement should be made prior to the hardening of the lozenge or candy but after the cough drop or candy has cooled somewhat, to avoid heat denaturation of the enzyme.

A lytic enzyme may be added to these substances in a liquid form or in a lyophilized state, whereupon it will be solubilized when it meets body fluids such as saliva. The enzyme may also be in a micelle or liposome.

The effective dosage rates or amounts of an altered or unaltered lytic enzyme to treat the infection will depend in part on whether the lytic enzyme will be used therapeutically or prophylactically, the duration of exposure of the recipient to the infectious bacteria, the size and weight of the individual, etc. The duration for use of the composition containing the enzyme also depends on whether the use is for prophylactic purposes, wherein the use may be hourly, daily or weekly, for a short time period, or whether the use will be for therapeutic purposes wherein a more intensive regimen of the use of the composition may be needed, such that usage may last for hours, days or weeks, and/or on a daily basis, or at timed intervals during the day. Any dosage form employed should provide for a minimum number of units for a minimum amount of time. The concentration of the active units of enzyme believed to provide for an effective amount or dosage of enzyme may be in the range of about 100 units/ml to about 500,000 units/ml of fluid in the wet or damp environment of the nasal and oral passages, and possibly in the range of about 100 units/ml to about 50,000 units/ml. More specifically, time exposure to the active enzyme units may influence the desired concentration of active enzyme units per ml. Carriers that are classified as "long" or "slow" release carriers (such as, for example, certain nasal sprays or lozenges) could possess or provide a lower concentration of active (enzyme) units per ml, but over a longer period of time, whereas a "short" or "fast" release carrier (such as, for example, a gargle) could possess or provide a high concentration of active (enzyme) units per ml, but over a shorter period of time. The amount of active units per ml and the duration of time of exposure depend on the nature of infection, whether treatment is to be prophylactic or therapeutic, and other variables. There are situations where it may be necessary to have a much higher unit/ml dosage, going as high as 10,000,000 units/ml.

The unaltered or "natural" version of the lytic enzyme may also be used or included in such compositions. The number of active units of each of the forms of the enzymes to be used or included in the composition may vary, depending on the use and composition contemplate. While the typical range of use of the enzymes may be from about 10,000 units/ml to about 500,000 units/ml, there may be a need for larger or smaller doses. For example, parenteral use may allow for very high amounts of the enzyme, such as up to $10^7$ units/ml. Doses may also be smaller than 10,000 units/ml, for example 100 units/ml.

The lytic enzyme should be in an environment having a pH which allows for activity of the lytic enzyme. If an individual has been exposed to someone with the upper respiratory disorder, the lytic enzyme will reside in the mucosal lining and prevent any colonization of the infecting bacteria. Prior to, or at the time the altered lytic enzyme is put in the carrier system or oral delivery mode, it is preferred that the enzyme be in a stabilizing buffer environment for maintaining a pH range between about 4.0 and about 9.0, more preferably between about 5.5 and about 7.5.

The stabilizing buffer should allow for the optimum activity of the lysin enzyme. The buffer may contain a reducing reagent, such as dithiothreitol. The stabilizing buffer may also be or include a metal chelating reagent, such as ethylenediaminetetracetic acid disodium salt, or it may also contain a phosphate or citrate-phosphate buffer, or any other buffer. The DNA coding of these phages and other phages may be altered to allow a recombinant enzyme to attack one cell wall at more than two locations, to allow the recombinant enzyme to cleave the cell wall of more than one species of bacteria, to allow the recombinant enzyme to attack other bacteria, or any combinations thereof. The type and number of alterations to a recombinant bacteriophage produced enzyme are incalculable.

A mild surfactant can be included in a therapeutic composition in an amount effective to potentiate the therapeutic effect of the altered lytic enzyme may be used in a therapeutic composition. Suitable mild surfactants include, inter alia, esters of polyoxyethylene sorbitan and fatty acids (Tween series), octylphenoxy polyethoxy ethanol (Triton-X series), n-Octyl-.beta.-D-glucopyranoside, n-Octyl-.beta.-D-thioglucopyranoside, n-Decyl-.beta.-D-glucopyranoside, n-Dodecyl-.beta.-D-glucopyranoside, and biologically occurring surfactants, e.g., fatty acids, glycerides, monoglycerides, deoxycholate and esters of deoxycholate. While this treatment may be used in any mammalian species, the preferred use of this product is for a human.

Additionally, the therapeutic composition may further comprise other enzymes, such as the enzyme lysostaphin for the treatment of any *Staphylococcus aureus* bacteria present along with the *S. pneumoniae*. Mucolytic peptides, such as lysostaphin, have been suggested to be efficacious in the treatment of *S. aureus* infections of humans (Schaffner et al., Yale J. Biol. & Med., 39:230 (1967) and bovine mastitis caused by *S. aureus* (Sears et al., J. Dairy Science, 71 (Suppl. 1): 244(1988)). Lysostaphin, a gene product of *Staphylococcus simulans*, exerts a bacteriostatic and bactericidal effect upon *S. aureus* by enzymatically degrading the polyglycine crosslinks of the cell wall (Browder et al., Res. Comm., 19: 393-400 (1965)). U.S. Pat. No. 3,278,378 describes fermentation methods for producing lysostaphin from culture media of *S. staphylolyticus*, later renamed *S. simulans*. Other methods for producing lysostaphin are further described in U.S. Pat. Nos. 3,398,056 and 3,594,284. The gene for lysostaphin has subsequently been cloned and sequenced (Recsei et al., Proc. Natl. Acad. Sci. USA, 84: 1127-1131 (1987)). The recombinant mucolytic bactericidal protein, such as r-lysostaphin, can potentially circumvent problems associated with current antibiotic therapy because of its targeted specificity, low toxicity and possible reduction of biologically active residues. Furthermore, lysostaphin is also active against non-dividing cells, while most antibiotics require actively dividing cells to mediate their effects (Dixon et al., Yale J. Biology and Medicine, 41: 62-68 (1968)). Lysostaphin, in combination with the altered lytic enzyme, can be used in the presence or absence of the listed antibiotics. There is a degree of added importance in using both lysostaphin and the lysin enzyme in the same therapeutic agent. Frequently, when a body has a bacterial infection, the infection by one genus of bacteria weakens the body or changes the bacterial flora of the body, allowing other potentially pathogenic bacteria to infect the body. One of the bacteria that sometimes co-infects a body is *Staphylococcus aureus*. Many strains of *Staphylococcus aureus* produce penicillinase, such that *Staphylococcus Streptococcus*, and other Gram positive bacterial strains will not be killed by standard antibiotics. Consequently, the use of the lysin and lysostaphin, possibly in combination with antibiotics, can serve as the most rapid and effective treatment of bacterial infections. A therapeutic composition may also include mutanolysin, and lysozyme.

Means of application of the therapeutic composition comprising a lytic enzyme include, but are not limited to direct, indirect, carrier and special means or any combination of means. Direct application of the lytic enzyme may be by nasal sprays, nasal drops, nasal ointments, nasal washes, nasal injections, nasal packings, bronchial sprays and inhalers, or indirectly through use of throat lozenges, mouthwashes or gargles, or through the use of ointments applied to the nasal nares, or the face or any combination of these and similar methods of application. The forms in which the lytic enzyme may be administered include but are not limited to lozenges, troches, candies, injectants, chewing gums, tablets, powders, sprays, liquids, ointments, and aerosols.

When the natural and/or altered lytic enzyme(s) is introduced directly by use of nasal sprays, nasal drops, nasal ointments, nasal washes, nasal injections, nasal packing, bronchial sprays, oral sprays, and inhalers, the enzyme is preferably in a liquid or gel environment, with the liquid acting as the carrier. A dry anhydrous version of the altered enzyme may be administered by the inhaler and bronchial spray, although a liquid form of delivery is preferred.

A composition comprising a lytic enzyme can be administered in the form of a candy, chewing gum, lozenge, troche, tablet, a powder, an aerosol, a liquid, a liquid spray, or toothpaste for the prevention or treatment of bacterial infections associated with upper respiratory tract illnesses. The unaltered lytic enzyme (also known as a "natural" enzyme) may be used alone or in conjunction with the chimeric and/or shuffled lytic enzyme(s). The lozenge, tablet, or gum into which the lytic enzyme, shuffled lytic enzyme and/or chimeric lytic enzyme, is added may contain sugar, corn syrup, a variety of dyes, non-sugar sweeteners, flavorings, any binders, or combinations thereof. Similarly, any gum-based products may contain acacia, carnauba wax, citric acid, cornstarch, food colorings, flavorings, non-sugar sweeteners, gelatin, glucose, glycerin, gum base, shellac, sodium saccharin, sugar, water, white wax, cellulose, other binders, and combinations thereof. Lozenges may further contain sucrose, cornstarch, acacia, gum tragacanth, anethole, linseed, oleoresin, mineral oil, and cellulose, other binders, and combinations thereof. Sugar substitutes can also be used in place of dextrose, sucrose, or other sugars.

For example, to treat a bacterial infection of the upper respiratory tract, the infection can be prophylactically or therapeutically treated with a composition comprising an effective amount of at least one lytic enzyme produced by a bacteria being infected with a bacteriophage specific for that bacteria, and a carrier for delivering the lytic enzyme to a mouth, throat, or nasal passage. The lytic enzyme is preferably a chimeric and/or shuffled lytic enzyme which may be used in conjunction with a holin protein or altered or unaltered phage associated lytic enzyme. Similarly, the natural or "unaltered" lytic enzyme may be used in conjunction with the chimeric and/or shuffled lytic enzymes, or it may be used alone. Similarly, the lytic enzymes may be used in combination with the holin protein(s). The lytic enzyme(s), the unaltered chimeric, and shuffled enzymes may be used alone or in any combination with the other, and may be used in any combination with the holin protein(s).

More specifically, a bacterial infection of the upper respiratory tract may be treated with a composition comprising an effective amount of at least one lytic enzyme specific for *S. pneumoniae*, for example Pal, and a carrier for delivering the lytic enzyme to a mouth, throat, or nasal passage. The lytic enzyme may be produced by directly infecting *Streptococcus pneumoniae* with a phage specific for *S. pneumoniae*, and producing a lytic enzyme specific for *S. pneumoniae*. Alternatively, the lytic enzyme may be produced by the recombinant methods. If an individual has been exposed to someone with the upper respiratory infection, the lytic enzyme may be applied to mucosal lining to prevent any colonization of the infecting bacteria.

Various combinations of one or more natural, chimeric or shuffled lytic enzymes are combined with a carrier which is placed in an inhaler to treat or prevent the spread of diseases localized in the mucus lining of the oral cavity, lungs, and nasopharynx. The lytic enzymes can be directed to the mucosal lining, where, in residence, they will be able to kill colonizing bacteria. Accordingly, a natural and/or chimeric and/or shuffled lytic enzyme, and/or its peptide fragments can be directed to the mucosal lining, where, in residence, they kill colonizing disease bacteria.

A lytic enzyme may also be placed in a nasal spray, wherein the spray is the carrier. The nasal spray can be a long acting or timed release spray, and can be manufactured by means well known in the art. An inhalant may also be used, so that the unaltered, chimeric and/or shuffled lytic enzyme may reach further down into the bronchial tract, including into the lungs.

The therapeutic composition which may be used for the prophylactic and therapeutic treatment of a *S. pneumoniae* infection includes the shuffled and/or chimeric enzyme and a means of application (such as a carrier system or an oral delivery mode) to the mucosal lining of the oral and nasal cavity, such that the enzyme is put in the carrier system or oral delivery mode to reach the mucosa lining. Of course, the natural lytic enzyme may be used alone or in combination with the "altered" lytic enzymes.

Compositions comprising lytic enzymes, or their peptide fragments can be directed to the mucosal lining, where, in residence, they kill colonizing disease bacteria. The mucosal lining, as disclosed and described herein, includes, for example, the upper and lower respiratory tract, eye, buccal cavity, nose, rectum, vagina, periodontal pocket, intestines and colon. Due to natural eliminating or cleansing mechanisms of mucosal tissues, conventional dosage forms are not retained at the application site for any significant length of time.

For these and other reasons, it is advantageous to have materials which exhibit adhesion to mucosal tissues, to be administered with one or more phage enzymes and other complementary agents over a period of time. Materials having controlled release capability are particularly desirable, and the use of sustained release mucoadhesives has received a significant degree of attention.

J. R. Robinson (U.S. Pat. No. 4,615,697, incorporated herein by reference) provides a good review of the various controlled release polymeric compositions used in mucosal drug delivery. The patent describes a controlled release treatment composition which includes a bioadhesive and an effective amount of a treating agent. The bioadhesive is a water swellable, but water insoluble fibrous, crosslinked, carboxy functional polymer containing (a) a plurality of repeating units of which at least about 80 percent contain at least one carboxyl functionality, and (b) about 0.05 to about 1.5 percent crosslinking agent substantially free from polyalkenyl polyether. While the polymers of Robinson are water swellable but insoluble, they are crosslinked, not thermoplastic, and are not as easy to formulate with active agents, and into the various dosage forms, as the copolymer systems of the present application. Micelles and multilamillar micelles may also be used to control the release of enzyme.

Other approaches involving mucoadhesives which are the combination of hydrophilic and hydrophobic materials, are known. Orahesive.RTM. from E.R. Squibb & Co is an adhesive which is a combination of pectin, gelatin, and sodium carboxymethyl cellulose in a tacky hydrocarbon polymer, for adhering to the oral mucosa. However, such physical mixtures of hydrophilic and hydrophobic components eventually fall apart. In contrast, the hydrophilic and hydrophobic domains in this application produce an insoluble copolymer.

U.S. Pat. No. 4,948,580, also incorporated by reference, describes a bioadhesive oral drug delivery system. The composition includes a freeze-dried polymer mixture formed of the copolymer poly(methyl vinyl ether/maleic anhydride) and gelatin, dispersed in an ointment base, such as mineral oil containing dispersed polyethylene. U.S. Pat. No. 5,413,792 (incorporated herein by reference) discloses paste-like preparations comprising (A) a paste-like base comprising a polyorganosiloxane and a water soluble polymeric material which are preferably present in a ratio by weight from 3:6 to 6:3, and (B) an active ingredient. U.S. Pat. No. 5,554,380 claims a solid or semisolid bioadherent orally ingestible drug delivery system containing a water-in-oil system having at least two phases. One phase comprises from about 25% to about 75% by volume of an internal hydrophilic phase and the other phase comprises from about 23% to about 75% by volume of an external hydrophobic phase, wherein the external hydrophobic phase is comprised of three components: (a) an emulsifier, (b) a glyceride ester, and (c) a wax material.

U.S. Pat. No. 5,942,243 describes some representative release materials useful for administering antibacterial agents, which are incorporated by reference.

Therapeutic compositions can also contain polymeric mucoadhesives including a graft copolymer comprising a hydrophilic main chain and hydrophobic graft chains for controlled release of biologically active agents. The graft copolymer is a reaction product of (1) a polystyrene macromonomer having an ethylenically unsaturated functional group, and (2) at least one hydrophilic acidic monomer having an ethylenically unsaturated functional group. The graft chains consist essentially of polystyrene, and the main polymer chain of hydrophilic monomeric moieties, some of which have acidic functionality. The weight percent of the polystyrene macromonomer in the graft copolymer is between about 1 and about 20% and the weight percent of the total hydrophilic monomer in the graft copolymer is between 80 and 99%, and wherein at least 10% of said total hydrophilic monomer is acidic, said graft copolymer when fully hydrated having an equilibrium water content of at least 90%.

Compositions containing the copolymers gradually hydrate by sorption of tissue fluids at the application site to yield a very soft jelly like mass exhibiting adhesion to the mucosal surface. During the period of time the composition is adhering to the mucosal surface, it provides sustained release of the pharmacologically active agent, which is absorbed by the mucosal tissue.

Mucoadhesivity of the compositions of this invention is, to a large extent, produced by the hydrophilic acidic monomers of the chain in the polystyrene graft copolymer. The acidic monomers include, but are not limited to, acrylic and methacrylic acids, 2-acrylamido-2-methyl-propane sulfonic acid, 2-sulfoethyl methacrylate, and vinyl phosphonic acid. Other copolymerizable monomers include, but are not limited to N,N-dimethylacrylamide, glyceryl methacrylate, polyethylene glycol monomethacrylate, etc.

The compositions of this application may optionally contain other polymeric materials, such as poly(acrylic acid), poly,-(vinyl pyrrolidone), and sodium carboxymethyl cellulose plasticizers, and other pharmaceutically acceptable excipients in amounts that do not cause deleterious effect upon mucoadhesivity of the composition. The dosage forms of the compositions of this invention can be prepared by conventional methods.

In cases where intramuscular injection is the chosen mode of administration, an isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. A vasoconstriction agent can be added to the formulation. The pharmaceutical preparations according to this application are provided sterile and pyrogen free.

A natural, chimeric and/or shuffled lytic enzyme may also be administered parenterally. For example, the lytic enzyme can be administered intramuscularly, intrathecally, subdermally, subcutaneously, or intravenously to treat infections by *Streptococcus pneumoniae*. In cases where parenteral injection is the chosen mode of administration, an isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. A vasoconstriction agent can be added to the formulation. The pharmaceutical preparations according to this application are provided sterile and pyrogen free.

The effective dosage rates or amounts of the lytic enzyme to be administered parenterally, and the duration of treatment will depend in part on the seriousness of the infection, the weight of the patient, the duration of exposure of the recipient to the infectious bacteria, the number of square centimeters of skin or tissue which are infected, the depth of the infection, the seriousness of the infection, and a variety of a number of other variables. The composition may be applied anywhere from once to several times a day, and may be applied for a short or long term period. The usage may last for days or weeks. Any dosage form employed should provide for a minimum number of units for a minimum amount of time. The concentration of the active units of enzymes believed to provide for an effective amount or dosage of enzymes may be selected as appropriate. The amount of active units per ml and the duration of time of exposure depend on the nature of infection, and the amount of contact the carrier allows the lytic enzymes to have. It is to be remembered that the enzyme works best when in a fluid environment. Hence, effectiveness of the enzymes is in part related to the amount of moisture trapped by the carrier.

Methods of treating various conditions are also provided, including methods of prophylactic treatment of *S. pneumoniae* infections, treatment of *S. pneumoniae* infections, reducing *S. pneumoniae* population or carriage, treating lower respiratory infection, treating ear infection, treating ottis media, treating endocarditis, treating contact lens solutions, and treating or preventing other local or systemic infections or conditions.

This invention may also be used to treat septicemia. For the treatment of a septicemic infection, for *pneumoniae*, or bacterial meningitis, there should be a continuous intravenous flow of therapeutic agent into the blood stream. The concentration of the enzymes for the treatment of septicemia is dependent upon the bacterial count in the blood and the blood volume.

Also provided is a method for treating *Streptococcus pneumoniae* infection, carriage or populations comprises treating the infection with a therapeutic agent comprising an effective amount of at least one lytic enzyme specific for *Streptococcus pneumoniae*. More specifically, a shuffled and/or chimeric lytic enzyme specific for lysing the cell wall of *Streptococcus pneumoniae* is produced from genetic material from a bacteriophage specific for *Streptococcus pneumoniae*.

One method for treating systemic or tissue bacterial infections caused by *Streptococcus pneumoniae* comprises parenterally treating the infection with a therapeutic agent comprising an effective amount of at least unaltered, shuffled or chimeric lytic enzyme specific for *S. pneumoniae*, and an appropriate carrier. A number of other different methods may be used to introduce the lytic enzyme(s). These methods include introducing the lytic enzyme intravenously, intramuscularly, subcutaneously, intrathecally, and subdermally. Intrathecal use would be most beneficial for treatment of bacterial meningitis.

Infections may be also be treated by injecting into the infected tissue of the patient a therapeutic agent comprising the appropriate unaltered, shuffled and/or chimeric lytic enzyme(s) and a carrier for the enzyme. The carrier may be comprised of distilled water, a saline solution, albumin, a serum, or any combinations thereof. More specifically, solutions for infusion or injection may be prepared in a conventional manner, e.g. with the addition of preservatives such as p-hydroxybenzoates or stabilizers such as alkali metal salts of ethylene-diamine tetraacetic acid, which may then be transferred into fusion vessels, injection vials or ampules. Alternatively, the compound for injection may be lyophilized either with or without the other ingredients and be solubilized in a buffered solution or distilled water, as appropriate, at the time of use. Non-aqueous vehicles such as fixed oils, liposomes, and ethyl oleate are also useful herein. Other phage associated lytic enzymes, along with a holin protein, may be included in the composition.

Various methods of treatment are provided for using a lytic enzyme as a prophylactic treatment for eliminating or reducing the carriage of *Pneumococci* bacteria, preventing those who have been exposed to others who have the symptoms of an infection from getting sick, or as a therapeutic treatment for those who have already become ill from the infection. Similarly, the natural, chimeric and/or shuffled lytic enzyme can be used to treat lower respiratory tract illnesses, particularly by the use of bronchial sprays intravenous administration of the enzyme.

Lower respiratory illness (i.e. *pneumoniae*) may be treated with the unaltered, chimeric and/or shuffled lytic enzyme for *Streptococcus pneumoniae*. Similar methods and techniques may be used to treat *pneumoniae* as was used to treat upper respiratory illnesses. Treatment may be more dependent on the use of inhalers and any other device or carrier which will get the lytic enzymes into the lungs. Additionally, to more effectively treat the *pneumoniae*, the enzyme should be given intravenously. As with the other treatment, the unaltered, chimeric, and/or shuffled lytic enzymes may be used.

A natural, shuffled and/or chimeric lytic enzyme can also be applied to the eye to treat an infection of *Streptococcus pneumoniae*. In one form of this invention, the enzyme is applied by means of eye drops. For example, a lytic enzyme can be used for the prophylactic and therapeutic treatment of eye infections, such as conjunctivitis. The method of treatment comprises administering eye drops or an eye wash which comprise an effective amount of at least one unaltered, chimeric and/or shuffled lytic enzymes genetically coded for by a bacteriophage specific for *Streptococcus pneumoniae* and a carrier capable of being safely applied to an eye, with the carrier containing the lytic enzymes. The eye drops or eye wash are preferably in the form of an isotonic solution. The pH of the solution should be adjusted so that there is no irritation of the eye, which in turn would lead to possible infection by other organisms, and possible to damage to the eye. While the pH range should be in the same range as for other lytic enzymes, the most optimal pH will be in the range of from 6.0 to 7.5. Similarly, buffers of the sort described above for the other lytic enzymes should also be used. Other antibiotics which are suitable for use in eye drops may be added to the composition containing the enzymes. Bactericides and bacteriostatic compounds may also be added. The concentration of the enzyme(s) in the solution can be in the range of from about 100 units/ml to about 500,000 units/ml, with a more preferred range of about 100 to about 5,000 units/mil, and about 100 to about 50,000 units/ml. Concentrations can be higher or lower than the ranges provided.

The lytic enzyme described above may also be used in a contact lens solution, for the soaking and cleaning of contact lenses. This solution, which is normally an isotonic solution, may contain, in addition to the enzyme, sodium chloride, mannitol and other sugar alcohols, borates, preservatives, and the like. A natural, shuffled and/or chimeric lytic enzyme can be included in a contact lens cleaning solution to treat or prevent infections by *Streptococcus pneumoniae*.

A natural, shuffled and/or chimeric lytic enzyme can also be administered to the ear of a patient. An unaltered, chimeric and/or shuffled enzyme may also be used to treat ear infections caused by *Streptococcus pneumoniae*. Otitis media is an inflammation of the middle ear characterized by symptoms such as otalgia, hearing loss and fever. One of the primary causes of these symptoms is a build up of fluid (effusion) in the middle ear. Complications include permanent hearing loss, perforation of the tympanic membrane, acquired cholesteatoma, mastoiditis, and adhesive otitis. Children who develop otitis media in the first years of life are at risk for recurrent acute or chronic disease. One of the primary causes of otitis media is *Streptococcus pneumoniae*. It is thought that *S. pneumoniae* causes otitis media by adhering to nasopharyngeal cells. The adherence of *S. pneumoniae* to nasopharyngeal cells causes those cells to become infected and to produce secretions. The middle ear becomes infected because mechanical or functional obstruction of the Eustachian tube, which protects the middle ear from nasopharyngeal secretions, results in negative middle ear pressure. This negative pressure causes the nasopharyngeal secretions to enter the middle ear resulting in an infection, such as otitis media, usually with effusion. The unaltered, shuffled and/or chimeric lytic enzyme (genetically coded for by a bacteriophage specific for *Streptococcus pneumoniae*, wherein the lytic enzyme specifically lyses the cell wall of said *Streptococcus pneumoniae*) may be applied to an infected ear by delivering the enzyme(s) in an appropriate carrier to the canal of the ear. The carrier may comprise sterile aqueous or oily solutions or suspensions. The lytic enzyme(s) may be added to the carrier, which may also contain suitable preservatives, and preferably a surface-active agent. Bactericidal and fungicidal agents preferably included in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol. Additionally, any number of other eardrop carriers may be used. The concentrations and preservatives used for the treatment of otitis media and other similar ear infections are the same as discussed for eye infections, and the carrier into which the enzyme goes is similar or identical to the carriers for treatment of eye infections. Additionally, the carrier may typically includes vitamins, minerals, carbohydrates, sugars, amino acids, proteinaceous materials, fatty acids, phospholipids, antioxidants, phenolic compounds, isotonic solutions, oil based solutions, oil based suspensions, and combinations thereof.

Endocarditis is commonly caused by Streptococcal infections, including *Streptococcus pneumoniae*. *Streptococcus pneumoniae*, as well as certain other Streptococcal species, may grow in the heart valves of an infected patient and cause damage thereto. Endocarditis is currently diagnosed by clinical features, echocardiogram, the presence of heart murmurs, and positive blood cultures. Patients with rheumatic fever, damaged heart valves or prosthetic valves are at risk of a secondary streptococcal infection leading to endocarditis when having routine dental or gastrointestinal procedures. Current therapy for endocarditis involves long term IV antibiotics; however, some of the antibiotics necessary to treat endocarditis are potentially toxic, such as vancomycin and gentamicin which may be nephrotoxic and ototoxic.

As an alternative or supplement to the use of antibiotics for endocarditis, an unaltered, chimeric and/or shuffled lytic enzyme may be used for the treatment of endocarditis. The enzyme may be preferably administered parenterally, and, perhaps under certain conditions, intramuscularly, subcutaneously, and subdermally. The carrier may be comprised of distilled water, a saline solution, albumin, a serum, or any combinations thereof. More specifically, solutions for infusion or injection may be prepared in a conventional manner, e.g. with the addition of preservatives such as p-hydroxybenzoates or stabilizers such as alkali metal salts of ethylenediamine tetraacetic acid, which may then be transferred into fusion vessels, injection vials or ampules. Alternatively, the compound for injection may be lyophilized either with or without the other ingredients and be solubilized in a buffered solution or distilled water, as appropriate, at the time of use. Non-aqueous vehicles such as fixed oils, liposomes, and ethyl oleate are also useful herein.

EXAMPLES

The following examples provide illustrations of certain embodiments of the invention and are not intended to be limiting of the scope of the invention.

Enzyme Purification Method

All chemicals were purchased from Sigma (St. Louis, Mo.) unless stated otherwise. *E. coli* were harvested by centrifugation, suspended in enzyme buffer (20 mM phosphate buffer (PB), 1 mM EDTA, 10 mM DTT) and broken by sonication for 1.5 min on ice. The crude extracts were ultracentrifuged (75,000 g for 1 h at 4° C.), the supernatant loaded on a DEAE-cellulose column (volume 20 ml) and washed with 3 volumes of 20 mM PB (pH 7.0), 4 volumes of PB containing 1 M NaCl, and 2 volumes of PB containing 0.1 M NaCl. The enzyme was eluted with PB containing 0.1 M NaCl and 6.5% (w/v) choline. Pooled fractions were dialyzed overnight (1:75) against enzyme buffer. Purification was verified by SDS-PAGE. Protein content was measured with the Bradford method using the dye reagent from Biorad (Hercules, Calif.).

Determination of Enzyme Unit (U)

*S. pneumoniae* strain DCC 1490 (serotype 14) was grown in brain heart infusion medium (BHI, Difco Laboratories, Detroit, Mich.) at 37° C. to log-phase, centrifuged at 5000 g for 10 min at 4° C., and resuspended in sterile saline to an absorbance at 600 nm of 1.3. Pal was diluted in enzyme buffer in serial 2-fold dilutions. In a 96-well plate 150 µl of the bacterial suspension was incubated with 150 µl of each Pal dilution (150 µl enzyme buffer for the control well). One unit of enzyme was defined as the reciprocal of the highest dilution, which caused a 50% decrease in absorbance after 15 min incubation at 37° C., as compared with the absorbance of the control well.

In Vitro Killing Assay

*Pneumococci* and *viridans streptococci* were grown in BHI and Todd-Hewitt broth with 1% yeast extract (Difco Laboratories, Detroit, Mich.) to stationary or log-phase, centrifuged and resuspended to an absorbance at 600 nm of 1.0. In a 96-well plate, 150 µl of the bacterial suspension were incubated with 150 µl of Pal (to a final concentration of 100, 1000 and 10000 U/ml) at 37° C. Samples were assayed in triplicates. At 30 sec, 10 l of each well was serially 10-fold diluted and plated on blood agar for titer determination. A control well contained 150 µl of the bacterial solution and 150 µl enzyme buffer. The bacterial titer of the control well was determined at time 0 and 10 min. Control titers at an absorbance of 1.0 varied slightly for each strain (Log10 7.0-8.95 cfu/ml). Groups were compared with the Mann-Whitney test. A p value<0.05 was considered significant.

Preparation of Samples for Electron Microscopy

*S. pneumoniae* strain DCC 1490 was grown in BHI to log-phase, centrifuged and resuspended in sterile saline to an absorbance at 600 nm of 1.0. 500 l of the suspension were incubated at room temperature with 500 µl of Pal at a final concentration of 50 U/ml. The lytic reaction was stopped after 10 sec, 1 min and 5 min by addition of glutaraldehyde (final concentration 2.5%). Bacteria and debris were pelleted by centrifugation and overlaid with 2.5% glutaraldehyde in 0.1 M cacodylate buffer (pH 7.4). The samples were then post-fixed in 1% osmium tetroxide, block stained with uranyl acetate and processed according to standard procedures by The Rockefeller University Electron Microscopy Service.

In vivo Nasal Infection Assay

*S. pneumoniae* strain DCC 1490 was grown to log-phase, centrifuged and resuspended to a predefined titer of 1010 cfu/ml. Swiss CD-1 mice (weight range 22 to 24 g, Charles River Laboratories, Wilmington, Mass.) were anesthetized with a mixture of ketamine (Fort Dodge Animal Health, Fort Dodge, Iowa, 1.2 mg/animal) and xylazine (Miles Inc., Shawnee Mission, Kans., 0.25 mg/animal), and inoculated in one nostril with 10 µl of the bacterial suspension (n=18) or 10 l of sterile saline (n=3). Fourty-two hours later, inoculated animals were again anesthetized and 25 l of Pal (350 U, n=9) or enzyme buffer (n=9) was instilled in each nostril over several minutes. The mouth of each animal was rinsed with additional 50 µl Pal (700 U). Five hours later, all animals were euthanized and the nasal cavity was washed through the dissected trachea with 60 µl of sterile saline. The nasal wash was serially 10-fold diluted and plated on blood agar for titer determination. The following day, a-hemolytic colonies were respread on blood agar and incubated with an optochin disk (BBL, Sparks, Md.). Bacteria with a zone of inhibition>14 mm were considered to be S. pneumoniae. Groups were compared with the Mann-Whitney test.

Resistance Assay

Exposure on agar plates: Strain DCC 1490 was grown in BHI to early log-phase, swabbed on blood agar plates and exposed to 10 µl of a low concentration of Pal (<10 U/ml). Colonies at the periphery of a clearing zone were picked, grown to log-phase, swabbed on a fresh plate and re-exposed to the same concentration of Pal. Exposure in liquid: Strain DCC 1490, grown to log-phase was harvested and suspended in saline to an OD at 600 nm of 1.0. One ml of bacteria was incubated with 1 ml of Pal at 1.5 U/ml for 2 min at 37(C (reducing the bacterial titer by Log10 0.7 cfu/ml). The reaction mixture with the surviving bacteria was then diluted 1:10 in fresh BHI and grown overnight. The next day the culture was again diluted 1:10 in fresh BHI, grown to log-phase as above and mixed with 15 U and 150 U in the following 2 rounds (reducing the titer by Log10 1.4 and 3.9 cfu/ml, respectively). After 16 rounds of exposure on agar or 3 rounds of exposure in liquid, susceptibility to Pal was tested using the in vitro killing assay (13), compared to the unexposed strain. Results were compared with the Mann-Whitney test. No significant difference could be shown.

Most strains of bacteria were grown at 30° C. in Luria broth (LB) or brain-heart infusion broth (BHI).

Many modifications and variations of the present disclosure are possible in light of the above teachings. Such other modifications and variations which will be readily apparent to a skilled are included within the spirit and scope of the attached claims. In the appended claims, articles such as "a," "an" and "the" may mean one or more than one unless indicated to the contrary. Claims that include "or" between one or more members of a group shall be deemed satisfied if one, more than one, or all of the group members are employed in a given product or process.

We claim:

1. An article of manufacture comprising a vessel containing a composition comprising an isolated polypeptide comprising the amino acid sequence of SEQ ID NO:1 and instructions for use of the composition in treatment of a patient exposed to or exhibiting symptoms consistent with exposure to *Streptococcus pneumoniae* bacteria, where the instructions for use of the composition indicate a method for using the composition, the method comprising the steps of:
   a. identifying the patient suspected of having been exposed to *Streptococcus pneumoniae*; and
   b. administering an effective amount of the composition to the patient.

2. The article of claim 1, wherein the isolated polypeptide is the-amino acid sequence of SEQ ID NO:1.

3. The article of claim 1, where the composition has killing activity against one or more bacteria strains selected from the group consisting of: *S. pneumoniae* DCC 1355, *S. pneumoniae* DCC 1335, *S. pneumoniae* DCC 1420, *S. pneumoniae* DCC 1476, *S. pneumoniae* DCC 1490, *S. pneumoniae* DCC 1494, *S. pneumoniae* DCC 1714, *S. pneumoniae* DCC 1808, *S. pneumoniae* DCC 1811, *S. pneumoniae* DCC 1850, *S. pneumoniae* AR 314, *S. pneumoniae* AR 620, *S. pneumoniae* GB 2017, *S. pneumoniae* GB 2092, *S. pneumoniae* GB 2163, *S. pneumoniae* R36A, and *S. pneumoniae* Lyt 4-4.

4. The article of claim 1, wherein the isolated polypeptide is a dry anhydrous lytic enzyme.

5. An article of manufacture comprising a packaging material and a therapeutic composition contained within the packaging material,
   a. the therapeutic composition comprising a Pal lytic enzyme that comprises the amino acid sequence of SEQ ID NO:1 where the Pal lytic enzyme is characterized by one or more of the following functions:
      an In vitro Killing Assay comprising treatment of an exponentially growing population of *S. pneumoniae* bacteria with 100 enzyme units (U) of the lytic enzyme per mL in an enzyme buffer for about 30 seconds results in a decrease in the viable titer of the *S. pneumoniae* bacteria by at least 3.3 in a $\log_{10}$ scale of colony forming units/ml, as compared to performing an In vitro Killing Assay using the enzyme buffer, where the enzyme buffer consists essentially of: 20 mM phosphate buffer (PB), 1 mM EDTA and 10 mM DTT alone;
      ii. an In vitro Killing Assay comprising treatment of a stationary phase of a population of *S. pneumoniae* bacteria with 10,000 enzyme units (U)/ml of the lytic enzyme in an enzyme buffer for about 30 seconds results in a decrease in the viable titer of the *S. pneumoniae* bacteria by at least 3.0 in a $\log_{10}$ scale of colony forming units/ml, as compared to perfoming an In vitro Killing Assay using the enzyme buffer, where the enzyme buffer consists essentially of: 20 mM phosphate buffer (PB), 1 mM EDTA and 10 mM DTT alone; and
      iii. an In vivo Nasal Infection Assay comprising administering about $10^8$ colony forming units of *S. pneumoniae* bacteria, followed by administration 42 hours later of about 1400 enzyme units (U) of the lytic enzyme results in a reduction of the *S. pneumoniae* population to 0 in a $\log_{10}$ scale/10 microliters nasal wash; and
   b. the packaging material comprising a label that indicates that the therapeutic composition can be used for treating one or more conditions selected from the group consisting of: exposure to *S. pneumoniae* bacteria, and infection by *S. pneumoniae* bacteria.

6. The article of claim 5, where the therapeutic composition has killing activity against one or more bacteria strains selected from the group consisting of: *S. pneumoniae* DCC 1355, *S. pneumoniae* DCC 1335, *S. pneumoniae* DCC 1420, *S. pneumoniae* DCC 1476, *S. pneumoniae* DCC 1490, *S. pneumoniae* DCC 1494, *S. pneumoniae* DCC 1714, *S. pneumoniae* DCC 1808, *S. pneumoniae* DCC 1811, *S. pneumoniae* DCC 1850, *S. pneumoniae* AR 314, *S. pneumoniae* AR 620, *S. pneumoniae* GB 2017, *S. pneumoniae* GB 2092, *S. pneumoniae* GB 2163, *S. pneumoniae* R36A, and *S. pneumoniae* Lyt 4-4.

7. A method of killing penicillin-resistant *S. pneumoniae* bacteria comprising the step of contacting the bacteria with a composition comprising an amount of an isolated polypeptide effective to kill the penicillin-resistant *S. pneumoniae* bacteria, the isolated polypeptide comprising the amino acid sequence of SEQ ID NO:1.

8. The method of claim 7, where the composition further comprises a carrier.

9. The method of claim 7, where the composition further comprises a suitable vehicle for delivery of the polypeptide to a site of infection.

10. The method of claim 7, where the composition further comprises an antibiotic.

11. The method of claim 7, wherein the isolated polypeptide is a Pal lytic enzyme.

12. The method of claim 7, wherein the composition comprises a carrier and about $50\text{-}10^7$ enzyme units (U) of the isolated polypeptide per mL of the composition.

13. The method of claim 7, wherein the isolated polypeptide is a Pal lytic enzyme characterized by at least one of the following functions:
   a. an In vitro Killing Assay comprising treatment of an exponentially growing population of *S. pneumoniae* bacteria with 100 U of the lytic enzyme for about 30 seconds results in a decrease in the viable titer of the *S. pneumoniae* bacteria by at least 3.3 in a $\log_{10}$ scale of colony forming units/ml, as compared to perfoming an In vitro Killing Assay using an enzyme buffer consisting essentially of: 20 mM phosphate buffer (PB), 1 mM EDTA and 10 mM DTT alone;
   b. an In vitro Killing Assay comprising treatment of a stationary phase of a population of *S. pneumoniae* bacteria with 10,000 U/ml of the lytic enzyme for about 30 seconds results in a decrease in the viable titer of the *S. pneumoniae* bacteria by at least 3.0 in a $\log_{10}$ scale of colony forming units/ml, as compared to perfoming an In vitro Killing Assay using an enzyme buffer consisting essentially of: 20 mM phosphate buffer (PB), 1 mM EDTA and 10 mM DTT alone; and
   c. an In vivo Nasal Infection Assay comprising administering about $10^8$ colony forming units of *S. pneumoniae* bacteria, followed by administration 42 hours later of about 1400 U of the lytic enzyme results in a reduction of the *S. pneumoniae* population to 0 in a $\log_{10}$ scale of colony forming units/10 µl nasal wash.

14. The method of claim 7, where the penicillin-resistant *S. pneumoniae* bacteria are selected from the group consisting of: *S. pneumoniae* Sp9-3, *S. pneumoniae* Sp14-3 and *S. pneumoniae* Sp23-1.

15. The method of claim 7, where the isolated polypeptide has lytic killing activity against one or more strains of bacteria selected from the group consisting of: *S. pneumoniae* R36A, and *S. pneumoniae* Lyt 4-4.

16. A method for reducing a population of capsule-deficient *S. pneumonia* bacteria comprising the step of contacting the bacteria with a composition comprising an amount of an isolated polypeptide effective to kill at least a portion of the capsule-deficient *S. pneumoniae* bacteria, the isolated polypeptide comprising the amino acid sequence of SEQ ID NO:1.

17. The method of claim 16, where the method further comprises contacting the bacteria with the composition a second time about 42 hours later.

18. The method of claim 16, where the composition further comprises a carrier and a vehicle for delivery of the polypeptide to a site of infection.

19. The method of claim 16, where the isolated polypeptide has lytic killing activity against one or more strains of bacteria selected from the group consisting of: *S. pneumoniae* R36A, and *S. pneumoniae* Lyt 4-4.

20. The method of claim 16, where the population of bacteria is an infection and the method further comprises the step of administering the isolated polypeptide to a subject having the infection.

21. A method for treating a penicillin-resistant *Streptococcus pneumoniae* infection comprising the step of administering to a subject, having a penicillin-resistant *Streptococcus pneumoniae* infection, an effective amount of a composition comprising an isolated polypeptide including the amino acid sequence of SEQ ID NO:1 and where the method is further characterized by one or more of the following:
   (a) the isolated polypeptide is a shuffled lytic enzyme, a chimeric lytic enzyme or a combination thereof
   (b) the composition further comprises a holin protein;
   (c) the composition is administered parenterally; and
   (d) the method is a method for treating endocarditis, thereby treating the penicillin-resistant infection.

22. The method of claim 21, where the isolated polypeptide has lytic killing activity against one or more strains of bacteria selected from the group consisting of: *S. pneumoniae* DCC 1355, *S. pneumoniae* DCC 1420, *S. pneumoniae* DCC 1494, *S. pneumoniae* R36A, and *S. pneumoniae* Lyt 4-4.

* * * * *

SEQUENCE LISTING

```
<160> NUMBER OF SEQ ID NOS: 2

<210> SEQ ID NO 1
<211> LENGTH: 296
<212> TYPE: PRT
<213> ORGANISM: Streptococcus pneumoniae

<400> SEQUENCE: 1

Met Gly Val Asp Ile Glu Lys Gly Val Ala Trp Met Gln Ala Arg Lys
1               5                   10                  15

Gly Arg Val Ser Tyr Ser Met Asp Phe Arg Asp Gly Pro Asp Ser Tyr
            20                  25                  30

Asp Cys Ser Ser Ser Met Tyr Tyr Ala Leu Arg Ser Ala Gly Ala Ser
        35                  40                  45

Ser Ala Gly Trp Ala Val Asn Thr Glu Tyr Met His Ala Trp Leu Ile
    50                  55                  60

Glu Asn Gly Tyr Glu Leu Ile Ser Glu Asn Ala Pro Trp Asp Ala Lys
65                  70                  75                  80

Arg Gly Asp Ile Phe Ile Trp Gly Arg Lys Gly Ala Ser Ala Gly Ala
                85                  90                  95

Gly Gly His Thr Gly Met Phe Ile Asp Ser Asp Asn Ile Ile His Cys
            100                 105                 110

Asn Tyr Ala Tyr Asp Gly Ile Ser Val Asn Asp His Asp Glu Arg Trp
        115                 120                 125

Tyr Tyr Ala Gly Gln Pro Tyr Tyr Val Tyr Arg Leu Thr Asn Ala
    130                 135                 140

Asn Ala Gln Pro Ala Glu Lys Lys Leu Gly Trp Gln Lys Asp Ala Thr
145                 150                 155                 160

Gly Phe Trp Tyr Ala Arg Ala Asn Gly Thr Tyr Pro Lys Asp Glu Phe
                165                 170                 175

Glu Tyr Ile Glu Glu Asn Lys Ser Trp Phe Tyr Phe Asp Asp Gln Gly
            180                 185                 190

Tyr Met Leu Ala Glu Lys Trp Leu Lys His Thr Asp Gly Asn Trp Tyr
        195                 200                 205

Trp Phe Asp Arg Asp Gly Tyr Met Ala Thr Ser Trp Lys Arg Ile Gly
```

```
              210                 215                 220
Glu Ser Trp Tyr Tyr Phe Asn Arg Asp Gly Ser Met Val Thr Gly Trp
225                 230                 235                 240

Ile Lys Tyr Tyr Asp Asn Trp Tyr Tyr Cys Asp Ala Thr Asn Gly Asp
                245                 250                 255

Met Lys Ser Asn Ala Phe Ile Arg Tyr Asn Asp Gly Trp Tyr Leu Leu
                260                 265                 270

Leu Pro Asp Gly Arg Leu Ala Asp Lys Pro Gln Phe Thr Val Glu Pro
        275                 280                 285

Asp Gly Leu Ile Thr Ala Lys Val
        290                 295

<210> SEQ ID NO 2
<211> LENGTH: 4735
<212> TYPE: DNA
<213> ORGANISM: Streptococcus pneumoniae

<400> SEQUENCE: 2
tttaaatttt ttgacaaagt taattcaaat tgtaccgctg aagcaatttt ccatgtattc      60
actcaaagtt gttcagtgtg ctcaatcat  attaaaatcg aacttggtaa tatctctact    120
ccttttagtg aagcagagga agaccttaaa tatcgaattg actcaaaagc cgatcaaaag    180
ctaactaacc aacagttgac ggcactcacg gaaaaggctc aactacatga cgcagaactg    240
aaagctaagg ctacaatgga gcagttaagt aacttagaaa aggcttatga aggtagaatg    300
aaagctaatg aagaagctat caacaaatcg gaacccgacc taatcttagc ggcaagtcga    360
attgaagcta ctatccaaga acttggcggg ctacgggaac tgaagaagtt cgtcgacagt    420
tgcatgagct cttctaatca aggtctaatt atcggtaaga acgacggtag ctctaccatt    480
aaggtatcaa gtgaccgaat ttctatgttc ccgcaggga  atgaagttat gtaccttacg    540
caagggttca ttcacatcga taacgggatc tttacccaat ccattcaagt cggccgattt    600
agaacggaac aatactcgtt taatccagac atgaacgtga ttcggtatgt aggataagga    660
gaataacatg acaaaattta tcaactcata cggccctctt cacttgaacc tttacgtcga    720
acaagttagt caggacgtaa cgaacaactc ctcgcgagtt agttggcgag ctactgtcga    780
ccgcgatgga gcttatcgaa cgtggactta tggaaatatt agtaacctt  ccgtatggtt    840
aaatggttca gtgttcata  gcagtcaccc agactacgac acgtccggcg aagaggtaac    900
gctcgcaagt ggagaagtga ctgttcctca caatagtgac gggacaaaga caatgtccgt    960
ttgggcttcg tttgacccta taacggcgt  tcacggaaat atcactatct ctactaatta   1020
cactttagac agtattccaa ggtctacaca gatttctagt tttgagggaa atcgaaatct   1080
aggatcttta catacggtta tctttaaccg aaaagtgaac tcttttacgc atcaagtttg   1140
gtaccgagtt ttcggtagcg actggataga tttaggtaag aaccatacta ctagcgtatc   1200
ctttacgccg tcactggact tagcaaggta cttacctaaa tcaagttccg gaacaatgga   1260
catctgtatt cgaacctata acggaactac gcaaattggt agtgacgtct attcaaacgg   1320
atggaggttc aacatccccg attcagtacg tcctactttt tcgggcattt ctttagtaga   1380
cacgacttca gcggttcgac agattttaac agggaacaac ttcctccaaa tcatgtcgaa   1440
cattcaagtc aacttcaaca atgcttccgg cgcttacgga tccactatcc aagcatttca   1500
cgctgagctc gtaggtaaaa accaagctat caacgaaaac ggcggcaaat tgggtatgat   1560
gaactttaat ggctccgcta ccgtaagagc atgggttaca gacacgcgag gaaaacaatc   1620
```

-continued

```
gaacgtccaa gacgtatcta tcaatgttat agaatactat ggaccgtcta tcaatttctc    1680
cgttcaacgt actcgtcaaa atcctgcaat tatccaagct cttcgaaatg ctaaggtcgc    1740
acctataacg gtaggaggtc aacagaaaaa catcatgcaa attaccttct ccgtggcgcc    1800
gttgaacact actaatttca cagaagatag aggttcggcg tcaggacgt tcactactat    1860
ttccctactg actaactcgt ccgcgaactt agctggtaac tacgggccgg acaagtctta    1920
catagttaag gctaaaatcc aagacaggtt cacttcgact gaatttagtg ctacggtacc    1980
taccgaatca gtagttctta actatgacaa ggacggtcga cttggagttg gtaaggttgt    2040
agaacaaggg aaggcagggt caattgatgc agcaggtaat atatatgctg gaggtcgaca    2100
agttcaacag tttcagctca ctgataataa tggagcattg aacaggggtc aatataacga    2160
tgttggaata agcgtgaaac agagtttaca tggcgaagta acaaatacga ggacaaccct    2220
acgggaactc gaggtgaatg gggactattt caaaatttct ggttagatag ctggaaaatg    2280
gttcaatcct tcattacaat gtcaggaaga atgttcatca ggacagcgaa cgatggaaac    2340
agctggagac ctaacaagtg gaaagaggtt ctatttaagc aagacttcga acagaataat    2400
tggcagaaac ttgttcttca agtgggtgg aaccatcact caacctatgg cgacgcattc    2460
tattcgaaaa ctcttgacgg catagtatat ttgagaggaa atgtgcataa aggacttatc    2520
gacaaagagg ctactattgc agtacttcct gaaggattta gaccgaaagt ttcaatgtat    2580
cttcaggctc tcaataactc atatggaaat gccattctat gtatatacac tgacggaaga    2640
cttgtggtga atcgaatgt agataattct tggttaaatt tagacaatgt ctcatttcgt    2700
atttaatttg agctgaaatc atgttataat attttttaga aaggaggtga gaactatgtt    2760
gaaccttaca aaatcgcgcc aaattgtggc agagttcact attggacaag gagctgaaaa    2820
gaaacttgtc aaaacaacga ttgtgaacat tgatgcaaac gcagtatcaa ccgtctctga    2880
aactcttcat gacccagact tgtatgctgc gaaccgtcga gaacttcgag ctgacgagca    2940
aaaacttcgc gaaactcgtt acgcaatcga agatgaaatt aatagctgga gcgggggaaa    3000
aaaggggggag cccggctcta acaggctgaa taaggaggcg tcaatctatg ccaatgtggc    3060
taaacgacac cgcagtcttg acgacgatta ttacagcgtg cagcggagtg cttactgtcc    3120
tactaaataa gttattcgaa tggaaatcga ataaagccaa gagcgttta gaggatatct    3180
ctacaactct tagcactctt aaacagcagg tcgacgggat tgaccaaacg acagtagcaa    3240
tcaatcacca aaatgacgtc attcaagacg gaactagaaa aattcaacgt taccgtcttt    3300
atcacgactt aaaagggaa gtgataacag gctatacaac tctcgaccat tttagagagc    3360
tctctatttt attcgaaagt tataagaacc ttggcggaaa tggtgaagtt gaagccttgt    3420
atgaaaaata caagaaatta ccaattaggg aggaagattt agatgaaact atctaacgaa    3480
caatatgacg tagcaaagaa cgtggtaacc gtagtcgttc cagcagcgat tgcactaatt    3540
acaggtcttg gagcgttgta tcaatttgac actactgcta tcacaggaac cattgcactt    3600
cttgcaactt ttgcaggtac tgttctagga gtttctagcc gaaactacca aaaggaacaa    3660
gaagctcaaa acaatgaggt ggaataatgg gagtcgatat tgaaaaaggc gttgcgtgga    3720
tgcaggcccg aaagggtcga gtatcttata gcatggactt tcgagacggt cctgatagct    3780
atgactgctc aagttctatg tactatgctc tccgctcagc ggagcttca agtgctggat    3840
gggcagtcaa tactgagtac atgcacgcat ggcttattga aaacggttat gaactaatta    3900
gtgaaaatgc tccgtgggat gctaaacgag gcgacatctt catctgggga cgcaaaggtg    3960
ctagcgcagg cgctggaggt catacaggga tgttcattga cagtgataac atcattcact    4020
```

```
gcaactacgc ctacgacgga atttccgtca acgaccacga tgagcgttgg tactatgcag      4080
gtcaacctta ctactacgtc tatcgcttga ctaacgcaaa tgctcaaccg gctgagaaga      4140
aacttggcty ycagaaagat gctactggtt tctggtacgc tcgagcaaac ggaacttatc      4200
caaaagatga gttcgagtat atcgaagaaa acaagtcttg gttctacttt gacgaccaag      4260
gctacatgct cgctgagaaa tggttgaaac atactgatgg aaattggtat tggttcgacc      4320
gtgacggata catggctacg tcatggaaac ggattggcga gtcatggtac tacttcaatc      4380
gcgatggttc aatggtaacc ggttggatta agtattacga taattggtat tattgtgatg      4440
ctaccaacgg cgacatgaaa tcgaatgcgt ttatccgtta taacgacggc tggtatctac      4500
tattaccgga cggacgtctg gcagataaac ctcaattcac cgtagagccg gacgggctca      4560
ttactgctaa agtttaaaat atagagagga ggaagctctt ttcttaatat tgtttctctt      4620
aatcccgcaa ggtttcgacc ctgcggggtt tatgtgtcgt gaattactct atttacttat      4680
tcgaagattt caattataat taaataatca acgagattca taattggagg aatga          4735
```